(12) United States Patent
Milton-Edwards

(10) Patent No.: US 10,971,035 B2
(45) Date of Patent: Apr. 6, 2021

(54) TRAINING IN DISPENSING A MEDICAMENT

(71) Applicant: Teva UK Limited, West Yorkshire (GB)

(72) Inventor: Mark Milton-Edwards, Cheshire (GB)

(73) Assignee: Teva UK Limited, West Yorkshire (GB)

( * ) Notice: Subject to any disclaimer, the term of this patent is extended or adjusted under 35 U.S.C. 154(b) by 471 days.

(21) Appl. No.: 15/862,903

(22) Filed: Jan. 5, 2018

(65) Prior Publication Data

US 2018/0130379 A1 May 10, 2018

Related U.S. Application Data

(63) Continuation of application No. 15/037,993, filed as application No. PCT/IB2015/002105 on Nov. 11, 2015, now abandoned.

(30) Foreign Application Priority Data

Nov. 11, 2014 (GB) .................................. 1420039

(51) Int. Cl.
| | | |
|---|---|---|
| *G09B 23/28* | (2006.01) | |
| *H04W 4/80* | (2018.01) | |
| *A61B 5/00* | (2006.01) | |
| *A61B 5/087* | (2006.01) | |
| *H04M 1/725* | (2021.01) | |
| *G09B 5/12* | (2006.01) | |

(Continued)

(52) U.S. Cl.
CPC .............. *G09B 23/28* (2013.01); *A61B 5/087* (2013.01); *A61B 5/6898* (2013.01); *G09B 5/125* (2013.01); *H04M 1/72522* (2013.01); *H04M 1/72544* (2013.01); *H04W 4/30* (2018.02); *H04W 4/80* (2018.02); *A61B 5/1118* (2013.01); *A61B 5/4848* (2013.01); *A61B 2562/0204* (2013.01); *A61B 2562/0219* (2013.01); *H04M 2250/12* (2013.01)

(58) Field of Classification Search
None
See application file for complete search history.

(56) References Cited

U.S. PATENT DOCUMENTS

| | | |
|---|---|---|
| 5,333,106 A | 7/1994 | Lanpher et al. |
| 5,839,429 A | 11/1998 | Marnfeldt et al. |
| 5,842,468 A | 12/1998 | Denyet et al. |

(Continued)

FOREIGN PATENT DOCUMENTS

| | | |
|---|---|---|
| EP | 1135056 B1 | 8/2006 |
| EP | 1992381 A1 | 11/2008 |

(Continued)

*Primary Examiner* — James B Hull
(74) *Attorney, Agent, or Firm* — Flaster Greenberg, P.C.

(57) ABSTRACT

A medicament-free device (e.g., a smartphone device) for simulating a medicament dispenser may include a sensing device and a processor. The sensing device may sense a user action performed upon the medicament-free device and may output sense data. The processor may receive the sense data, compare the sense data with predefined data, and provide feedback based on how the sense data compares to the predefined data. The predefined data may be indicative of a model user action associated with the medicament dispenser.

20 Claims, 18 Drawing Sheets

(51) Int. Cl.
*H04W 4/30* (2018.01)
*A61B 5/11* (2006.01)

(56) References Cited

U.S. PATENT DOCUMENTS

| | | | |
|---|---|---|---|
| 5,887,586 A | 3/1999 | Dahlback et al. | |
| 6,285,731 B1 | 9/2001 | Marnfeldt et al. | |
| 6,390,088 B1 | 5/2002 | Sprenger et al. | |
| 6,958,691 B1 | 10/2005 | Anderson et al. | |
| 6,978,780 B1 | 12/2005 | Marnfeldt et al. | |
| 6,990,975 B1 | 1/2006 | Jones et al. | |
| 7,072,738 B2 | 7/2006 | Bonney et al. | |
| 7,151,456 B2 | 12/2006 | Godfrey et al. | |
| 7,191,777 B2 | 3/2007 | Brand et al. | |
| 7,198,172 B2 | 4/2007 | Harvey et al. | |
| 7,233,228 B2 | 6/2007 | Lintell et al. | |
| 7,249,687 B2 | 7/2007 | Anderson et al. | |
| 7,347,200 B2 | 3/2008 | Jones et al. | |
| 7,383,837 B2 | 6/2008 | Robertson et al. | |
| 7,424,888 B2 | 9/2008 | Harvey et al. | |
| 7,495,546 B2 | 2/2009 | Lintell et al. | |
| 7,837,648 B2 | 11/2010 | Blair et al. | |
| 8,231,573 B2 | 7/2012 | Edwards et al. | |
| 8,240,301 B2 | 8/2012 | Spaargaren et al. | |
| 8,424,517 B2 | 4/2013 | Sutherland et al. | |
| 8,462,109 B2 | 6/2013 | Nasiri et al. | |
| 8,464,707 B2 | 6/2013 | Jongejan et al. | |
| 8,474,452 B2 | 7/2013 | Gumaste et al. | |
| 8,547,239 B2 | 10/2013 | Peatfield et al. | |
| 8,807,131 B1 | 8/2014 | Tunnell et al. | |
| 8,960,189 B2 | 2/2015 | Morrison et al. | |
| 8,997,735 B2 | 4/2015 | Zierenberg et al. | |
| 9,056,174 B2 | 6/2015 | Bradshaw et al. | |
| 9,162,031 B2 | 10/2015 | Gumaste et al. | |
| 9,174,009 B2 | 11/2015 | Peatfield et al. | |
| 9,188,579 B2 | 11/2015 | Shen et al. | |
| 9,242,056 B2 | 1/2016 | Andersen et al. | |
| 9,339,616 B2 | 5/2016 | Denny et al. | |
| 9,352,107 B2 | 5/2016 | Von Hollen et al. | |
| 9,364,619 B2 | 6/2016 | Overfield et al. | |
| 9,427,534 B2 | 8/2016 | Bruin et al. | |
| 9,463,291 B2 | 10/2016 | Imran et al. | |
| 9,468,729 B2 | 10/2016 | Sutherland et al. | |
| 9,550,031 B2 | 1/2017 | Van Sickle et al. | |
| 9,694,147 B2 | 7/2017 | Peatfield et al. | |
| 9,736,642 B2 | 8/2017 | Ostrander et al. | |
| 9,764,104 B2 | 9/2017 | Gumaste et al. | |
| 9,839,398 B2 | 12/2017 | Yamamori et al. | |
| 9,911,308 B2 | 3/2018 | Edwards et al. | |
| 9,956,360 B2 | 5/2018 | Germinario et al. | |
| 9,962,507 B2 | 5/2018 | Germinario et al. | |
| 9,962,508 B2 | 5/2018 | Bruin et al. | |
| 10,016,134 B2 | 7/2018 | Hansen et al. | |
| 10,046,121 B2 | 8/2018 | Kolb et al. | |
| 10,258,753 B2 | 4/2019 | Adams et al. | |
| 10,272,215 B2 | 4/2019 | Adams et al. | |
| 10,391,270 B2 | 8/2019 | Adams et al. | |
| 10,688,261 B2 | 6/2020 | Van Sickle et al. | |
| 2002/0185128 A1 | 12/2002 | Theobald et al. | |
| 2003/0192535 A1 | 10/2003 | Christrup et al. | |
| 2004/0089299 A1 | 5/2004 | Bonney et al. | |
| 2004/0117062 A1 | 6/2004 | Bonney et al. | |
| 2005/0119604 A1 | 6/2005 | Bonney et al. | |
| 2005/0161467 A1 | 7/2005 | Jones et al. | |
| 2005/0247312 A1 | 11/2005 | Davies et al. | |
| 2005/0251289 A1 | 11/2005 | Bonney et al. | |
| 2007/0111175 A1 | 5/2007 | Raven et al. | |
| 2008/0059133 A1 | 3/2008 | Edwards et al. | |
| 2008/0160492 A1 | 7/2008 | Campbell et al. | |
| 2008/0230057 A1 | 9/2008 | Sutherland et al. | |
| 2009/0156952 A1 | 6/2009 | Hunter et al. | |
| 2009/0221308 A1 | 9/2009 | Lerner et al. | |
| 2010/0234064 A1 | 9/2010 | Harris, Jr. | |
| 2010/0242960 A1 | 9/2010 | Zangerle et al. | |
| 2010/0250280 A1 | 9/2010 | Sutherland et al. | |
| 2011/0282693 A1 | 11/2011 | Craft et al. | |
| 2012/0116241 A1 | 5/2012 | Shieh et al. | |
| 2012/0143073 A1 | 6/2012 | Denyer et al. | |
| 2013/0269685 A1 | 10/2013 | Wachtel et al. | |
| 2014/0106324 A1* | 4/2014 | Adams | A61B 5/6898 434/262 |
| 2014/0182584 A1 | 7/2014 | Sutherland et al. | |
| 2014/0322682 A1* | 10/2014 | Baym | G09B 7/02 434/219 |
| 2015/0126888 A1 | 5/2015 | Patel et al. | |
| 2015/0283341 A1* | 10/2015 | Adams | A61M 15/0021 128/202.22 |
| 2015/0339953 A1 | 11/2015 | Shah | |
| 2016/0082208 A1 | 3/2016 | Ballam et al. | |
| 2016/0128389 A1 | 5/2016 | Lamb et al. | |
| 2016/0166766 A1 | 6/2016 | Schuster et al. | |
| 2016/0193432 A1 | 7/2016 | Harris et al. | |
| 2016/0228657 A1 | 8/2016 | Sutherland et al. | |
| 2016/0256639 A1 | 9/2016 | Van Sickle et al. | |
| 2016/0314256 A1 | 10/2016 | Su et al. | |
| 2016/0325058 A1* | 11/2016 | Samson | A61B 5/087 |
| 2017/0079557 A1 | 3/2017 | Lauk et al. | |
| 2017/0109493 A1 | 4/2017 | Hogg et al. | |
| 2017/0140125 A1 | 5/2017 | Hogg et al. | |
| 2017/0164892 A1 | 6/2017 | Sezan et al. | |
| 2017/0173279 A1 | 6/2017 | Sutherland et al. | |
| 2017/0246406 A1 | 8/2017 | Sutherland et al. | |
| 2017/0258993 A1 | 9/2017 | Pizzochero et al. | |
| 2017/0262613 A1 | 9/2017 | Ljungberg et al. | |
| 2017/0325734 A1 | 11/2017 | Sutherland et al. | |
| 2017/0363673 A1 | 12/2017 | Mukherjee et al. | |
| 2018/0011988 A1 | 1/2018 | Ziegler et al. | |
| 2018/0052964 A1 | 2/2018 | Adelson et al. | |
| 2018/0085540 A1 | 3/2018 | Dantsker et al. | |
| 2018/0125365 A1 | 5/2018 | Hunter et al. | |
| 2018/0161530 A1 | 6/2018 | Ganton et al. | |

FOREIGN PATENT DOCUMENTS

| | | |
|---|---|---|
| EP | 3228345 A1 | 10/2017 |
| JP | H05333106 A | 12/1993 |
| JP | 2000181496 A | 6/2000 |
| JP | 2009514605 A | 4/2009 |
| JP | 2009125077 A | 6/2009 |
| JP | 2009273663 A | 11/2009 |
| JP | 2012507802 A | 3/2012 |
| JP | 2013501566 A | 1/2013 |
| JP | 2013516265 A | 5/2013 |
| JP | 2015536691 A | 12/2015 |
| WO | WO/1995/022365 A1 | 8/1995 |
| WO | WO 1995/022365 A1 | 8/1995 |
| WO | WO 1999/063901 A1 | 12/1999 |
| WO | WO/1999/063901 A1 | 12/1999 |
| WO | WO 02-69496 A1 | 11/2000 |
| WO | WO 2003/063754 A1 | 8/2003 |
| WO | WO/2003/063754 A1 | 8/2003 |
| WO | WO/2009/003989 A1 | 1/2009 |
| WO | WO 2009/003989 A1 | 1/2009 |
| WO | WO 2014/037843 A1 | 3/2014 |
| WO | WO/2016/043601 A1 | 3/2016 |
| WO | WO/2017/005605 A1 | 1/2017 |
| WO | WO/2017/051389 A1 | 3/2017 |
| WO | WO/2017/129521 A1 | 8/2017 |
| WO | WO/2017/141194 A1 | 8/2017 |
| WO | WO/2017/176693 A1 | 10/2017 |
| WO | WO/2017/176704 A1 | 10/2017 |
| WO | WO/2017/180980 A1 | 10/2017 |
| WO | WO/2017/189712 A1 | 11/2017 |
| WO | WO/2018/128976 A1 | 7/2018 |
| WO | WO/2018/134552 A1 | 7/2018 |
| WO | WO/2018/134553 A1 | 7/2018 |

\* cited by examiner

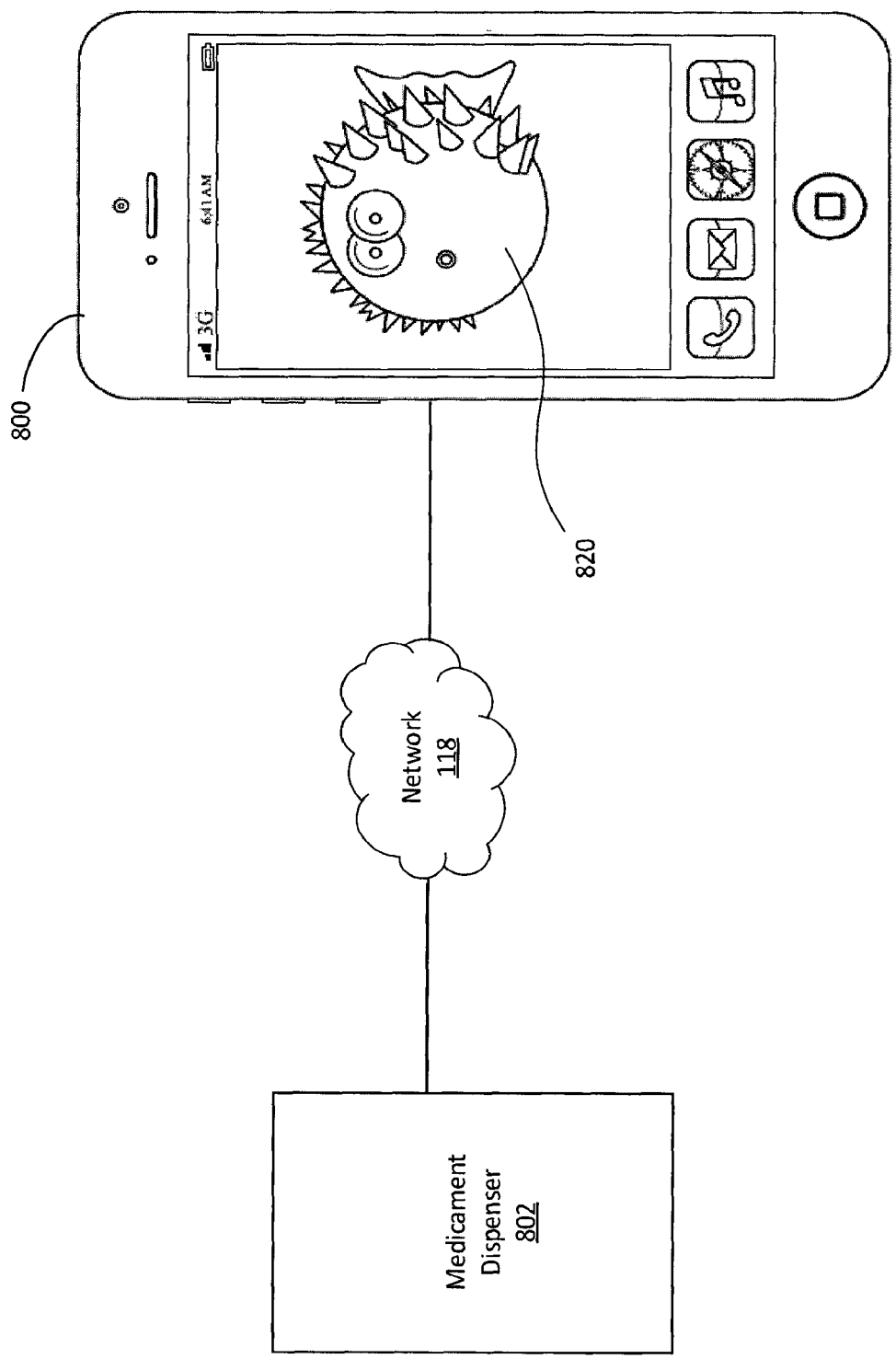

TRAINING IN DISPENSING A MEDICAMENT

CROSS REFERENCE TO RELATED APPLICATIONS

This application is a continuation of U.S. patent application Ser. No. 15/037,993, filed May 19, 2016, which is the National Stage Entry under 35 U.S.C. § 371 Patent Cooperation Treaty Application No. PCT/IB2015/002105, filed Nov. 11, 2015, which claims the benefit of Great Britain Application No. 1420039.8 filed on Nov. 11, 2014, which his incorporated herein by reference as if fully set forth.

BACKGROUND

It is important that patients properly adhere to medicament usage advice. For example, adhering to advice regarding medicament usage with respect to prescribed and/or recommended techniques of dispensing a medicament may be a significant factor in improving the results of medical treatments. Non-adherence to medicament usage advice may negatively affect health outcomes and the effectiveness of therapeutics.

SUMMARY

A mobile smartphone device for simulating a medicament dispenser may include
a microphone; a display; and a processor. The processor may be configured to cause the display to display a representation of a type of oral inhaler; receive a signal from the microphone indicative of user's airflow; determine, based on the signal, whether the airflow would be sufficient for dispensing medicament from the type of oral inhaler represented; and provide feedback to a user based on the determination.

A medicament-free device for simulating a medicament dispenser may include a sensing device and a processor. The sensing device may sense a user action performed upon the medicament-free device and may output sense data. The processor may receive the sense data, compare the sense data with predefined data, and provide feedback based on how the sense data compares to the predefined data. The predefined data may be indicative of a model user action associated with the medicament dispenser.

A system for simulating a medicament dispenser may include a medicament dispenser configured to dispense a medicament and a medicament-free device for simulating the medicament dispenser. The medicament-free device may include a sensing device configured to sense a user action performed upon the medicament-free device and to output sense data; and a processor. The processor may receive the sense data; compare the sense data with predefined data indicative of a model user action associated with the medicament dispenser; and provide feedback based on how the sense data compares to the predefined data.

BRIEF DESCRIPTION OF THE DRAWINGS

FIG. 8A illustrates an example use of a medicament dispenser providing input illustrated by an example GUI on the mobile device.

DESCRIPTION

It is important that patients adhere to medicament usage advice. A factor that may contribute to non-adherence of prescribed and/or recommended uses of medicament may be a lack of feedback and/or immediate indication of how the medicament is being dispensed and/or used (e.g., lack of feedback of whether the medicament is being dispensed and/or used correctly and/or incorrectly). This may apply to the treatment of chronic conditions, the use of medicament having slow-acting effects, the use of medicament for maintenance, and so forth. Promoting and/or encouraging increased compliance and adherence with the dispensing of medicament among users (e.g., by providing feedback, such as instant rewards) may be provided. For example, promotion and/or encouragement of compliance with the use of a medication dispenser related to childhood asthma may be provided.

Sixty percent of all puffs from devices (e.g., inhalers) used to dispense asthma medicament may be ineffective, e.g., because of incorrect usage. Flawed inhaler techniques may be commonly attributed to incorrect inhalation, exhalation, and/or positioning of the medicament dispenser body and/or head. Combining competition and/or rewards with "smart" device connectivity and inhaler training devices and applications may serve to improve adherence and health outcomes, e.g., through effective delivery of medicament into the lungs, rather than the mouth and stomach.

A system, method, and instrumentality may be provided for training a user in administering a medicament, e.g., administering a medicament from a dispenser. A user may be trained in the administering of a medicament from a simulated and/or actual medicament dispenser. A number of different types of medicament dispensers may be simulated, and/or the medicament dispensers may be compatible with various medical devices (e.g., as new devices are developed). A number of interconnected and/or widely available communication devices may be provided to provide multi-platform access of medicament dispenser data to a large user base. Feedback may be received in response to a user's operation of the simulated and/or actual medicament dispenser. Monitoring user actions, visualizing user actions, connecting data, and/or visualizing other information may provide a solution for training patients in the use of a variety of medicament dispenser types, and/or in providing actionable data to users and medical professionals for improving adherence, efficacy, and/or impact analysis of medicament usage.

Figure 1:
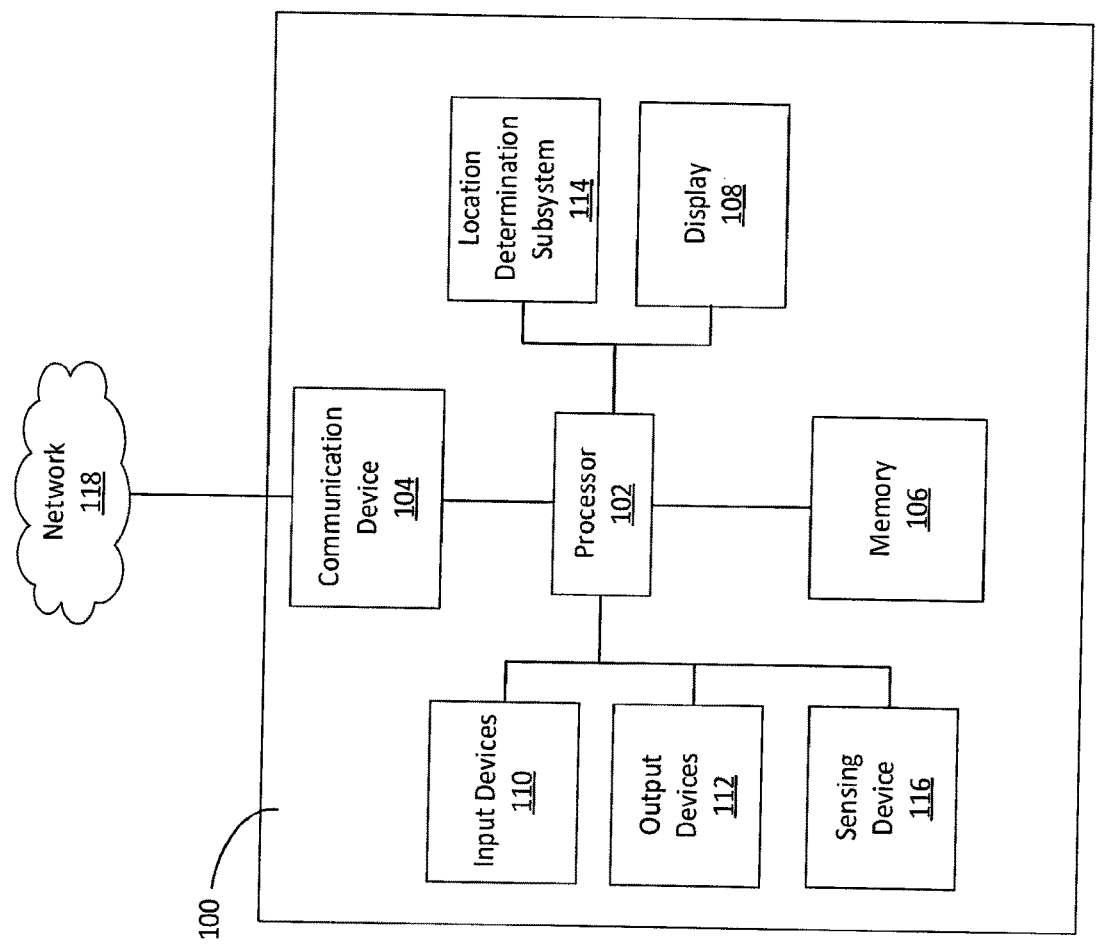
FIG. 1 is a block diagram of an example mobile device.

FIG. 1 depicts an example mobile device 100 that may be used to provide training for using a medicament dispenser. The mobile device 100 may be configured to execute an application (e.g., a computer application) capable of receiving and/or analyzing data representative of an interaction with a user and/or presenting training information to the user. The application may simulate an actual use of a defined medicament dispenser. The mobile device 100 may include a personal computer, such as a laptop or desktop computer, a tablet device, a cellular phone or smartphone, a server, or another type of mobile device. The mobile device 100 may include a processor 102, a communication device 104, a memory 106, a display 108, input devices 110, output devices 112, a location determination subsystem 114, a sensing device 116, and/or the like. The mobile device 100 may include additional, different, or fewer components, and each of the components may include one, or more, other components. For example, an input device 110 and/or an output device 112 may include a sensing device 116, etc.

The processor 102 may include one or more general purpose processors, special purpose processors, conventional processors, digital signal processors (DSPs), microprocessors, integrated circuits, a programmable logic device (PLD), application specific integrated circuits (ASICs), or the like. The processor 102 may perform signal coding, data processing, image processing, power control, input/output processing, and/or any other functionality that enables the mobile device 100 to perform as described herein.

The processor 102 may store information in, and/or retrieve information from, the memory 106. The memory 106 may include a non-removable memory and/or a removable memory. The non-removable memory may include random-access memory (RAM), read-only memory (ROM), a hard disk, or any other type of non-removable memory storage. The removable memory may include a subscriber identity module (SIM) card, a memory stick, a memory card, or any other type of removable memory. The memory may be local memory or remote memory external to the mobile device 100. The memory 106 may store instructions which are executable by the processor 102. Different information may be stored in different locations in the memory 106. For example, the memory 106 may store instructions that when executed by processor 102 perform the methods disclosed herein, e.g., the methods described in FIG. 10.

The processor 102 may communicate with other devices via the communication device 104. The communication device 104 may transmit and/or receive information over the network 118, which may include one or more other mobile devices. The communication device 104 may perform wireless and/or wired communications. The communication device 104 may include a receiver, transmitter, transceiver, or other device capable of performing wireless communications via an antenna. The communication device 104 may be capable of communicating via one or more protocols, such as a cellular communication protocol, a Wi-Fi communication protocol, Bluetooth®, Bluetooth® Low Energy (e.g., Bluetooth® Smart), a near field communication (NFC) protocol, an internet protocol, another proprietary protocol, or any other radio frequency (RF) or communications protocol. The mobile device 100 may include one or more communication devices 104.

The processor 102 may be in communication with a display 108 for providing information to a user. The information may be provided via a user interface on the display 108. The information may be provided as an image generated on the display 108. The display 108 and the processor 102 may be in two-way communication, as the display 106 may include a touch-screen device capable of receiving information from a user and providing such information to the processor 102.

The processor 102 may be in communication with a location determination subsystem 114 (e.g., GPS, cellular location determination, and/or Wi-Fi) for receiving geospatial information. The processor 102 may be capable of determining the GPS coordinates of the wireless communication device 100 based on the geospatial information received from the location determination subsystem 114. The geospatial information may be communicated to one or more other communication devices to identify the location of the mobile device 100.

The processor 102 may be in communication with input devices 110 and/or output devices 112. The input devices 110 may include a camera, a microphone, a keyboard or other buttons or keys, and/or other types of input devices for sending information to the processor 102. The display 108 may be a type of input device, as the display 108 may include touch-screen sensor capable of sending information to the processor 102. The output devices 112 may include speakers, indicator lights, or other output devices capable of receiving signals from the processor 102 and providing output from the mobile device 100. The display 108 may be a type of output device, as the display 108 may provide images or other visual display of information received from the processor 102.

The processor 102 may be in communication with sensing device 116. Sensing device 116 may include one, or more, sensing devices 116. Sensing device 116 may be internal to mobile device 100, and/or sensing device 116 may be external to mobile device 100. For example, sensing device 116 may be a peripheral sensing device that provides functionality to the mobile device 100, e.g., functionality for detecting physical signals and/or activities that a user may place upon a mobile device 100. The sensing device 116 may be comprised of a sensor and/or a group of sensors configured to monitor user actions and/or dispensing data (e.g., data that is representative of a how a medicament dispenser is operated by a user).

The sensing device 116 may be an electronic device that converts physical properties into an electronic signal. The sensing device 116 may include an acoustic sensor, a pressure sensor, an accelerometer, a biological sensor (e.g., a biosensor), and the like. For example, an acoustic sensor may be used to convert sound waves into an electronic signal, a pressure sensor may be used to convert pressure into an electronic signal, and/or an accelerometer may be used to convert orientation and movement (e.g., acceleration) into an electronic signal. A biosensor may include a transducer and a biological element (e.g., an enzyme, an antibody, a nucleic acid, and the like). The biological element may interact with an analyte (e.g., an analyte being tested by the transducer), and a resulting biological response may be converted into an electronic signal. The sensing device 116 and/or sensor may include a communications device.

The mobile device 100 may be configured to communicate with the sensing device 116 and/or to provide information (e.g., information based upon dispensing data) with the sensing device 116. The sensing device 116 and/or the mobile device 100 may communicate by way of wired and/or wireless (e.g., radio) signals. The mobile device 100 and/or sensing device 116 may analyze the data with respect to the quality of the user's administering technique and present the resulting information to a user based upon the analysis.

As shown on FIG. 2A-2D, a mobile device 200 may provide a simulated demonstration of a medicament dispenser. The mobile device 200 may provide the simulated medicament dispenser via an application running on the mobile device 200. The simulated medicament dispenser may be illustrated in static form and/or in animated form on the mobile device's display. The simulated medicament dispenser 202 may comprise an oral inhaler, an injector, a dermal applicator, a pill dispenser, and the like.

The type of medicament dispenser 202 may be characterized by the shape and/or size of the medicament dispenser 202, the type of medicament dispensed by the medicament dispenser 202, the electronics and/or sensors resident in the medicament dispenser 202, and so forth. For example, a first medicament dispenser and a second medicament dispenser may be oral inhaler devices. The first medicament dispenser and the second medicament dispenser may have similar inhaler housings (e.g., the size and/or shape of the inhaler housings of the first and second medicament dispensers may be similar). The first medicament dispenser and the second medicament dispenser may comprise the same, or different, types of medicaments. For example, the medicament in the first medicament dispenser may comprise a stronger dose of medicament than comprised in the second medicament dispenser. The first medicament dispenser and second medicament dispenser may require different activities for medical dispensing, for example, in the example wherein the first and second medicament dispensers have similar housings but comprise different medicaments. The first medicament dispenser and second medicament dispenser requiring different activities for medical dispensing may require different demonstrations of medicament dispensers 202.

Figure 2A:
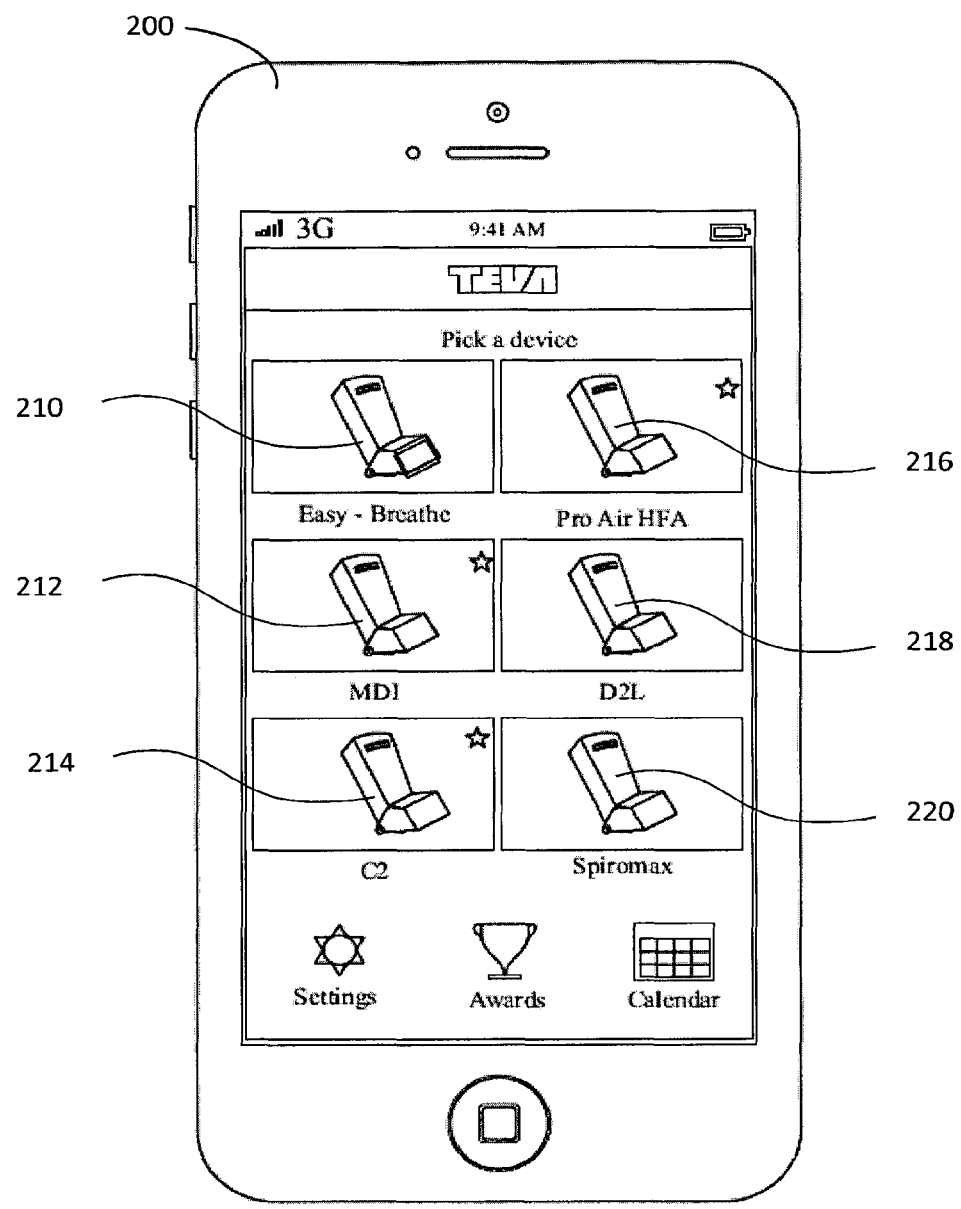
FIG. 2A is an example GUI showing multiple example medicament dispensers.

Training a user in administering a medicament from a variety of types of dispensers may be provided. As shown in FIG. 2A, the mobile device 200 may allow a user to choose a medicament dispenser, for the simulated demonstration. The mobile device 200 may provide a visual representation of a medicament device for choosing. For example, the mobile device 200 may provide a visual of an Easy Breathe device 210, ProAir device 216, Spiromax device 220, etc. A user may select a medicament device via input, e.g., via touch. The mobile device 200 may provide information about the medicament dispenser (e.g., textual descriptions and/or ratings of the medicament dispenser).

Figure 2B:
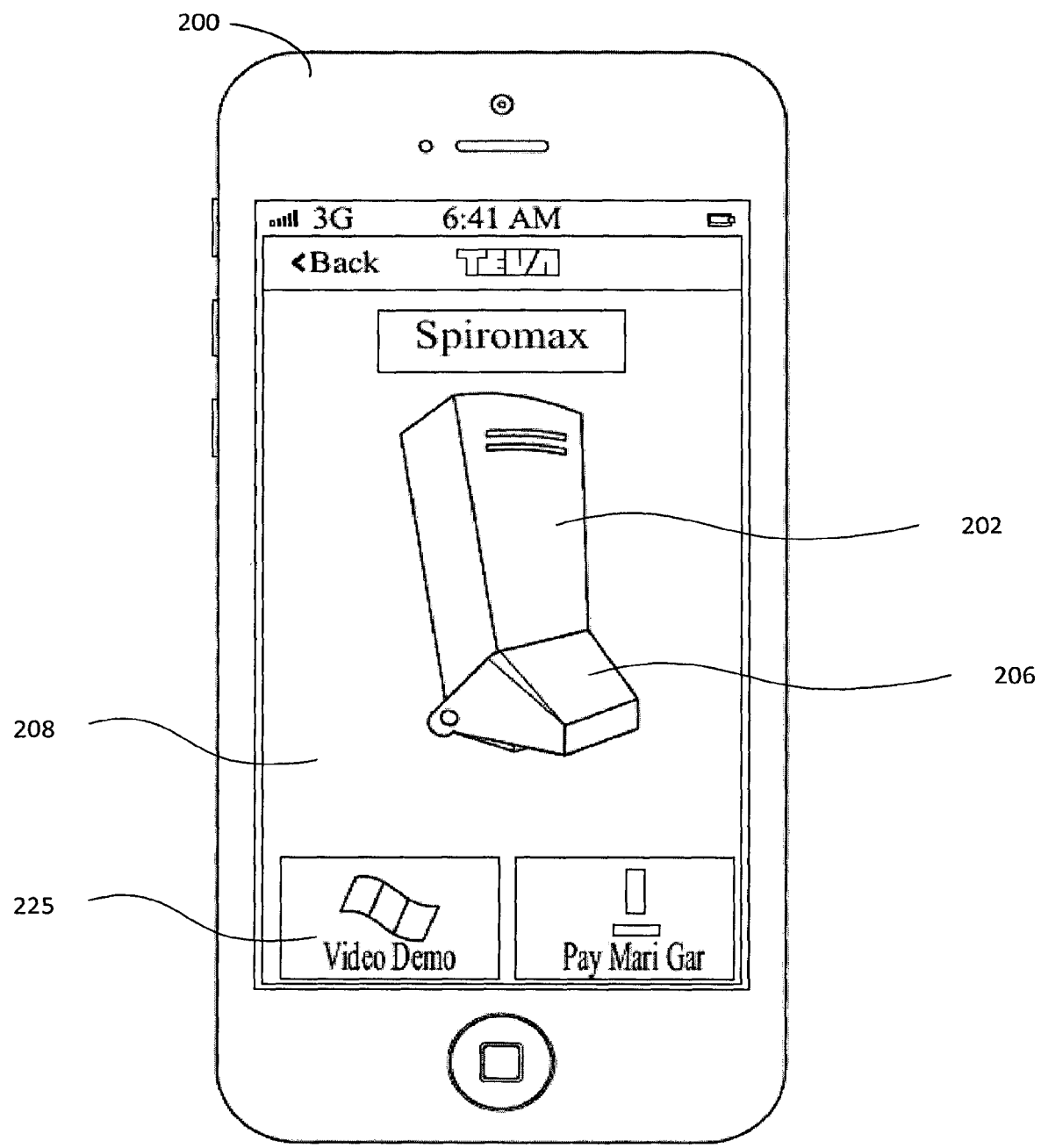
FIG. 2B is an example GUI providing a demonstration of an example medicament dispenser.
Figure 2C:
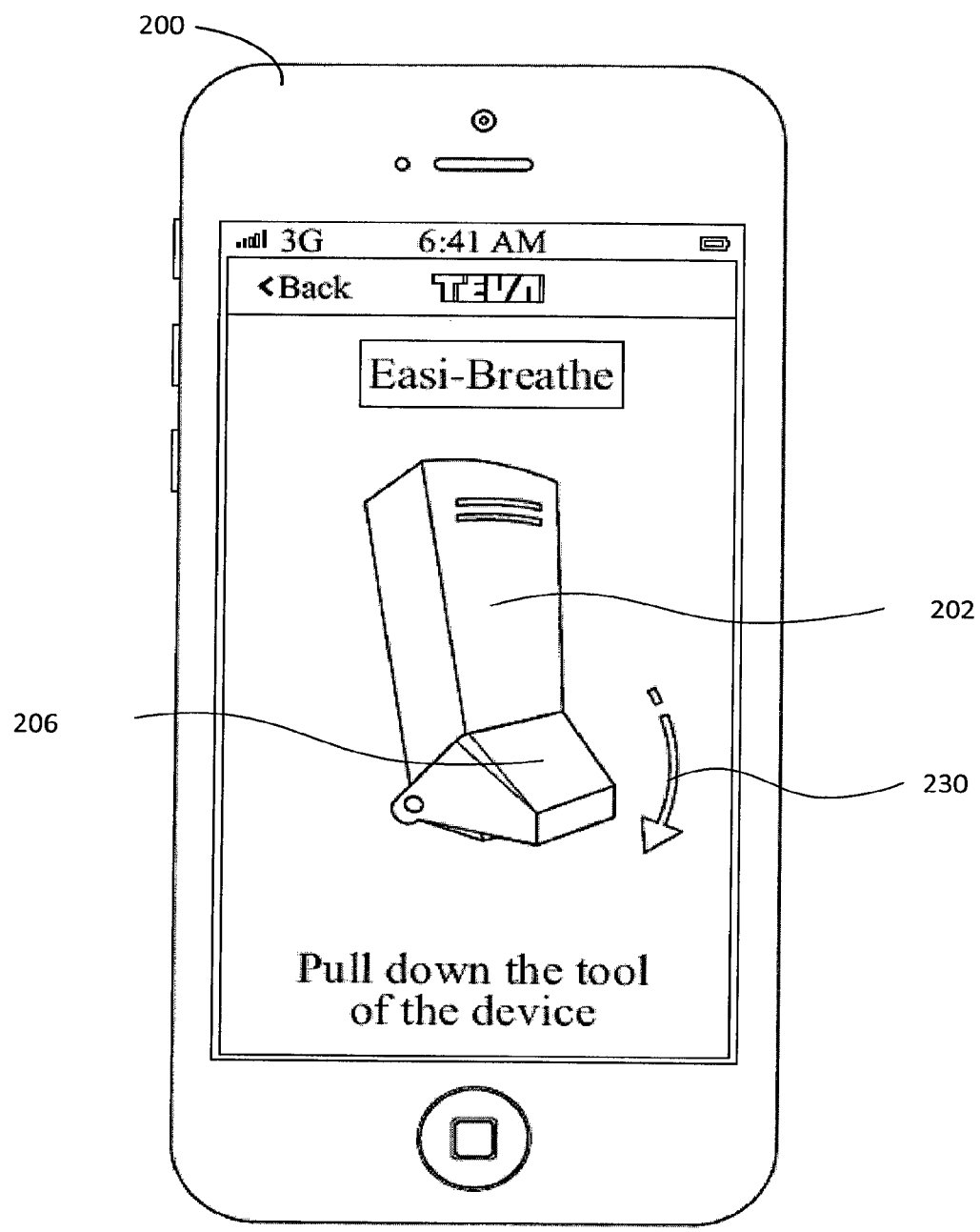
FIG. 2C is an example GUI providing another demonstration of an example medicament dispenser.

As shown on FIGS. 2B and 2C, a demonstration button 225 may provide different views (e.g., top view, bottom view, side views, inside views, etc.) of the medicament dispenser 202. The demonstration may allow a user to perform a demonstration of the medicament dispenser 202 and/or to see a demonstration of the medicament dispenser 202 in use. The mobile device 200 may allow a user to perform actions required to dispense a medicament from the medicament dispenser 202. For example, the mobile device 200 may allow a user to open a cap 206 of the medicament dispenser 202, perform a dispensing activity (e.g., inhalation, exhalation, shaking, etc.) to the medicament dispenser 202, and/or close the cap 206 of the medicament dispenser 202. The mobile device 200 may provide an indication (e.g., feedback) if one or more dispensing activities is missed and/or performed incorrectly. For example, the mobile device 200 may indicate if the cap 206 is not closed after the dispensing activity is performed. The mobile device 200 may allow a user to watch a video of the medicament dispenser 202 being used properly and/or improperly. The mobile device 200 may allow a user to watch the video of the medicament dispenser 202 being used properly and/or improperly, for example, in response to the user improperly demonstrating the medicament dispenser 202 (e.g., the user not closing the cap 206 after performing a medicament dispensing activity), and/or the mobile device 200 may allow a user to watch the video of the medicament dispenser 202 being used properly and/or improperly based on a selection by the user. The mobile device may allow a user to see different views of different medicament dispensers 202, e.g., for comparison purposes.

Figure 2D:
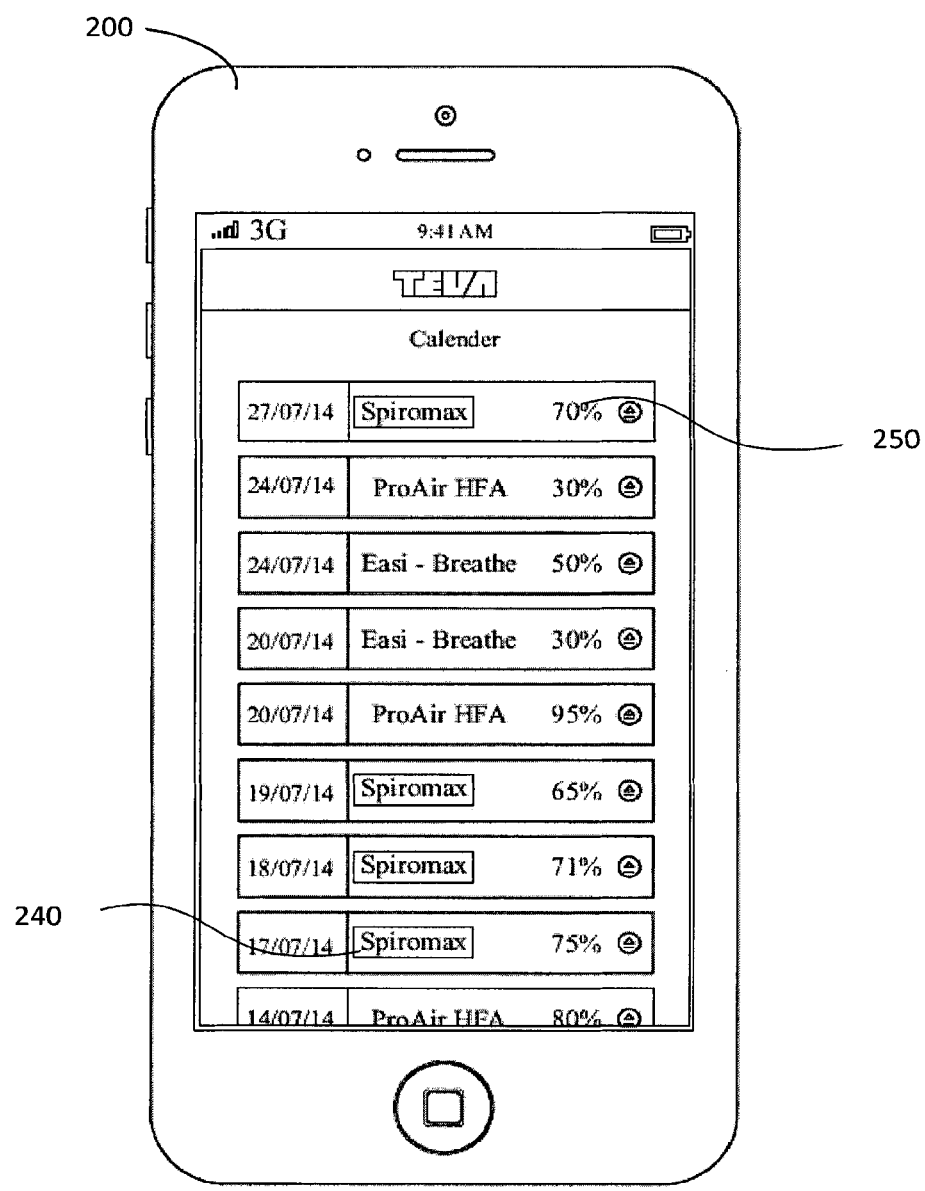
FIG. 2D is an example GUI providing a scoring information relating to an example medicament dispenser.

As shown on FIG. 2D, and described herein, the mobile device 200 may provide scores 250 of a use of the simulated medicament dispenser 202. The scores 250 may be previous scores of the user and/or previous scores of other users. The scores 250 may represent actions performed by the user, as the actions may compare with actions providing optimal results of medicament dispensing. The scores 250 may be based on a demonstration provided by the user, such as the demonstration described above. For example, a user may obtain a score 250 based on performing all activities required for dispensing a medicament (e.g., opening cap 206, performing a dispensing activity, and/or closing cap 206). The score may be reduced if the user misses a required medicament dispensing activity (e.g., the user does not close the cap 206 after the medicament is dispensed). Each of the medicament dispensing activities may be rated and/or scaled. For example, opening the cap 206 may be weighted differently, and/or similarly, as performing a dispensing activity or closing cap 206. An optimum score may be reached if the user performs all activities required for dispensing a medicament, and/or performs each activities at an optimum level.

Figure 3:
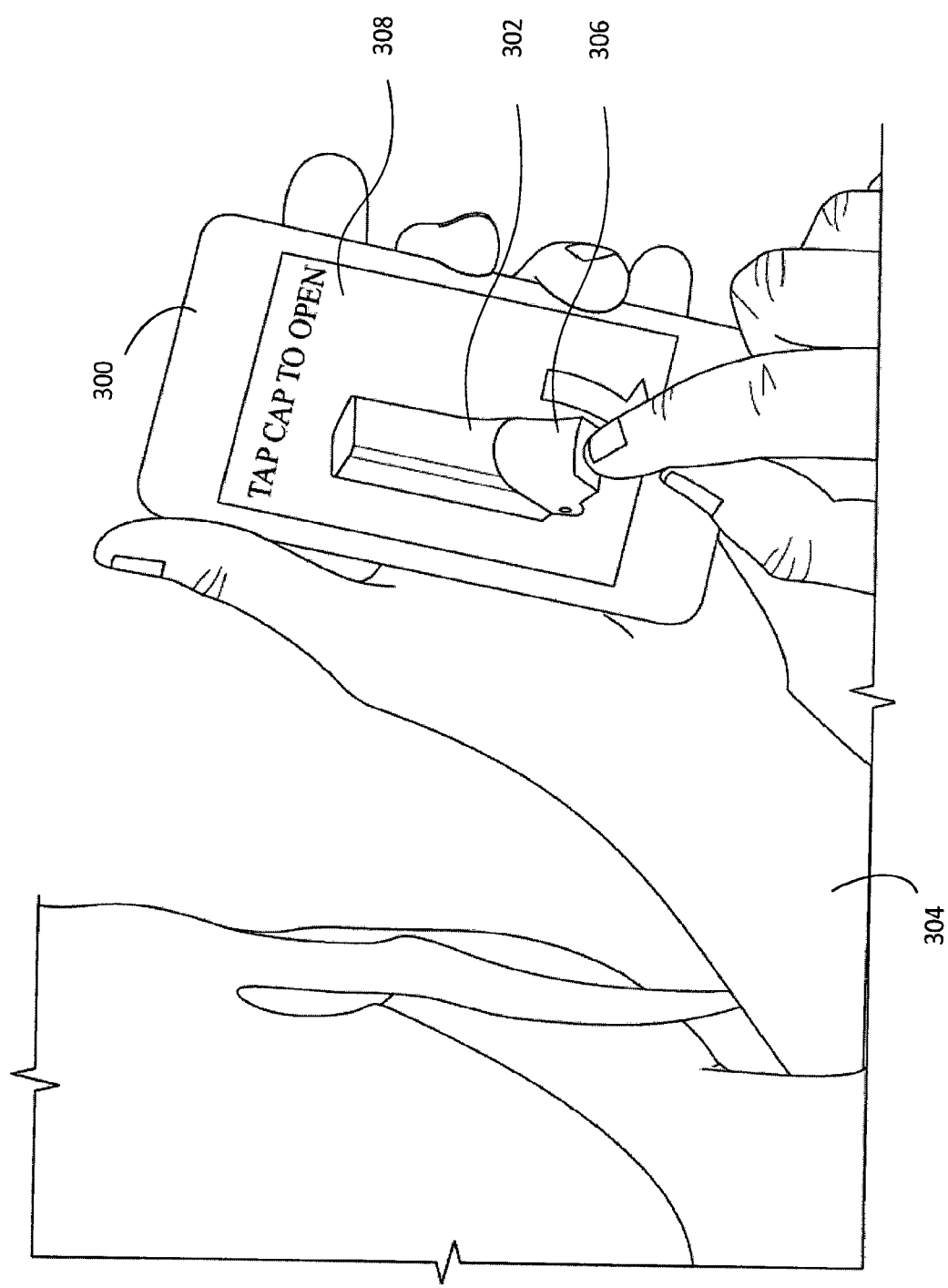
FIG. 3 illustrates an example use of a simulated medicament dispenser, via touch.

As shown on FIG. 3, a user 304 may provide input to a mobile device 300. A user 304 may interact with the mobile device 300 using many and various forms. For example, the user 304 may physically touch (e.g., using an input device 308, such as a touchscreen) the mobile device 300 to interact with the mobile device 300 and/or the user 304 may interact with mobile device 300 via voice commands. The touchscreen 308 may comprise a touch sensor allowing the user to interact with the mobile device 300, e.g., by touching areas of the display. The touchscreen 308 may display visual information to a user.

The user 304 may perform tests of one or more simulated medicament dispensers. For example, as shown on FIG. 3, a user choosing an inhaler as the simulated medicament dispenser 302, may open and/or close a cap 306 of the simulated medicament dispenser 302, e.g., by swiping across the touchscreen 308 of the mobile device 300. The user 304 may observe portions (e.g., front, back, bottom, top portions) of the simulated medicament dispenser 302, e.g., to compare one simulated medicament dispenser 302 with other medicament dispensers. Actions that a user 304 performs on a mobile device 300 that correlates with a medicament dispenser activity may be prompted and/or demonstrated by on-screen visuals.

The mobile device 300 and/or sensing device may be configured to detect, measure, and/or process various physical properties, conditions, and/or changes performed upon the mobile device 300. For example, the sensing device may detect physical properties (e.g., signals) of actions performed on the mobile device 300. The mobile device 300 and/or sensing device may convert the physical signals performed on the mobile device 300 to electronic signals. The actions performed on the mobile device 300 may be correlated with actions performed on a medicament device.

A user 304 may apply an action to the mobile device 300, such as shaking the mobile device 300. The mobile device 300 may include one or more integrated accelerometers that may determine the movement (e.g., shaking) performed upon the mobile device 300. The mobile device 300 and/or the sensing device, for example, may determine whether the user 304 performed an adequate shaking of the mobile device 300, as the shaking simulates the movement required to prepare a medicament dispenser (e.g., inhaler). The mobile device 300 may provide feedback of the user's shaking of the mobile device 300, e.g., by indicating whether the user 304 adequately shook the mobile device 300. By permitting a user to simulate the shaking of the medicament dispenser 302, via mobile device 300, the user 304 can practice such action and be provided with immediate feedback of the action. Other user actions, e.g., tapping of the mobile device 300 to correspond with a button click on the corresponding medicament dispenser 302, may be simulated on the mobile device 300.

An accelerometer may be used to determine the orientation of the mobile device 300 while the medicament dispenser 302 is being simulated, e.g., whether a user 304 is holding the mobile device 300 in a manner that would provide optimal medicament release from the simulated medicament dispenser 302. A user 304 holding an actual medicament dispenser improperly, e.g., while inhaling from the device, may not receive a sufficient dosage of the medicament. The accelerometer may be configured to detect the orientation and/or movement of the mobile device when the user 304 is simulating taking the medicament. For example, the accelerometer may determine that the mobile device 300 is tilted too far to the right when the mobile device 300 is simulating inhaling medicament from an inhaler. The mobile device 300 may provide feedback to the user 304 that the mobile device 300 was tilted too far to the right, for example. The mobile device 300 may indicate to the user that the orientation of the mobile device 300 is optimal, sub-optimal, etc. The mobile device 300 may indicate suggestions to the user 304 for correcting the non-optimal orientation and/or movements performed upon the mobile device 300. The accelerometer may be used in real time to provide an audio and/or visual indication of whether the user 304 is holding the mobile device 300 in a manner that corresponds to the optimal use of the medicament dispenser (e.g., inhaler). For example, the mobile device 300 may include a pleasant beeping sound when the user holds the mobile device 300 in an optimal position, and the mobile device 300 may present a buzzing sound when the user 304 is holding the mobile device 300 in an incorrect orientation.

Monitoring of medicament dispensing data may be provided. Parameters monitored by the sensing device and/or the mobile device may effectively represent the properties (e.g., flow rate, breathing patterns, dosage, etc.) of a use of an actual medicament dispenser (e.g., an inhaler). Dispensing data may be representative of a technique with which a user may administer a medicament from a medicament dispenser. The dispensing data may include data representing a physical action executed by a user in operating the medicament dispenser; a fluid pressure; a spatial orientation of the medicament dispenser; an acceleration applied to the medicament dispenser; a quantity of medicament dispensed; and/or a rate at which medicament is dispensed. The user's technique may be captured by the sensing device and/or mobile device and/or recorded as dispensing data, e.g., by detecting and/or measuring data representing various physical properties. Obtaining a qualitative or quantitative measure of the user's technique may provide assessments and/or training.

The mobile device may be configured to process the medicament dispensing data in accordance with predetermined data so as to generate assessed data. The predetermined data may include data representative of an optimal mode and/or an ideal usage technique and/or pattern in which a medicament dispenser may be operated by a user. The predetermined data may be downloaded data, and/or may have been prescribed by a medication provider or medical professional. For example, when the mode is adhered to by a user, it optimizes the effectiveness of the dispensed medicament. The mobile device may perform processes and/or computations performed by sophisticated electronic components found within a medicament dispenser. The mobile device may contain the requisite electronic components. This configuration may provide cost savings in the manufacturing of a medicament dispenser.

Figure 4:
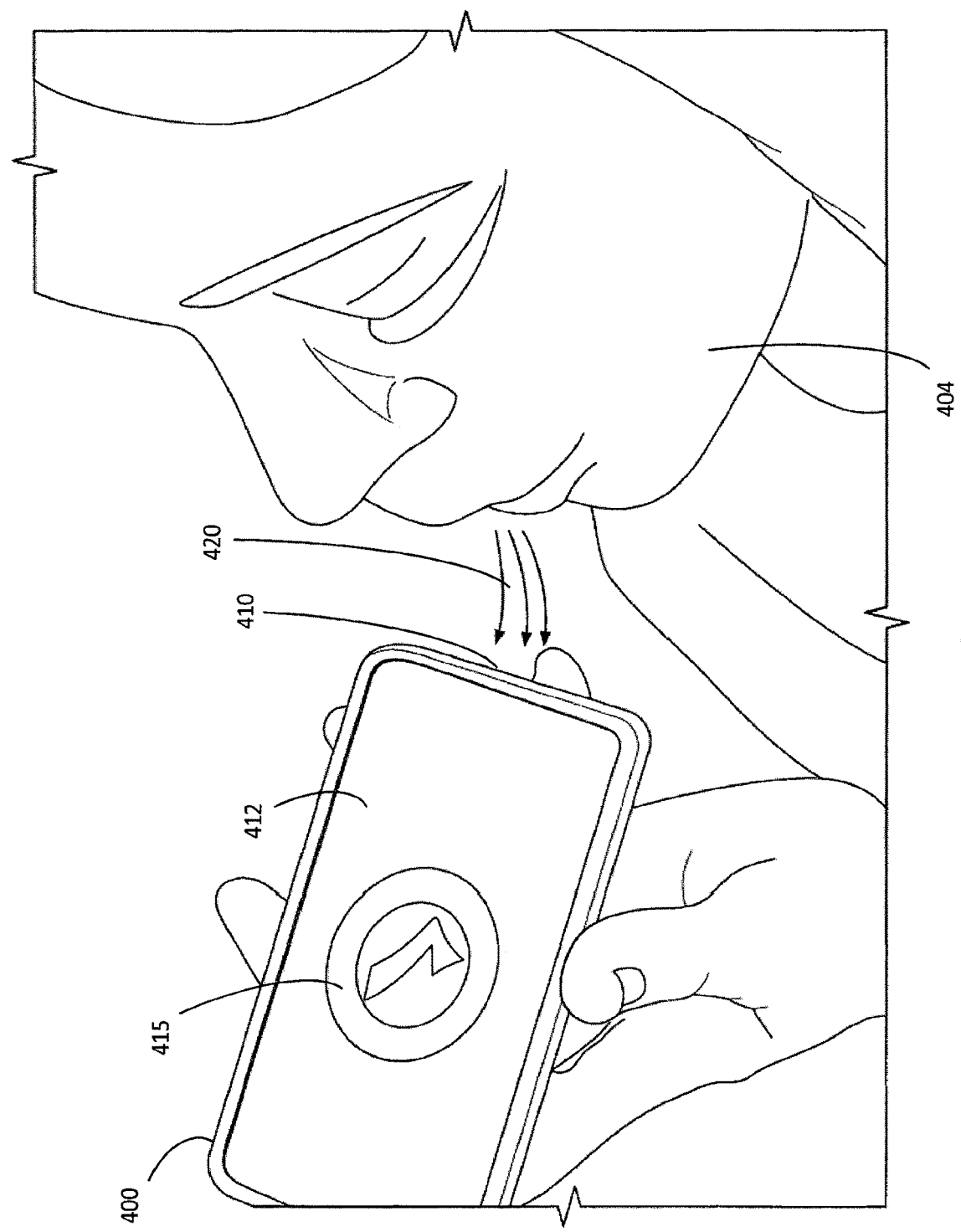
FIG. 4 illustrates an example use of a simulated medicament dispenser, via exhalation and/or inhalation.

As shown on FIG. 4, a user 404 may obtain medicament dispenser data by exhaling and/or inhaling 420 proximate to input device 410 (e.g., microphone) of mobile device 400. The input device 410 (e.g., microphone) may be configured to detect the acoustic signal of a user 404 inhaling and/or exhaling 420. The mobile device 400 may be configured to distinguish a user's 404 inhale from a user's exhale, and vice-versa. For example, software and/or hardware resident on the mobile device 400 may be used to determine that a user's 404 expelled breath is an exhale. The mobile device 400 may provide an indication to the user 404 (e.g., an indication via display 108) of whether the user's activity was an inhale and/or exhale. The mobile device 400 may provide an indication to the user 404 of whether the user's activity is the activity expected by the mobile device 400. For example, the mobile device 400 may provide an indication to the user 404 that the user 404 inhaled when, for example, the user 404 was expected to exhale. The mobile device 400 may provide an indication to the user 404 that the user 404 exhaled when, for example, the user 404 was expected to inhale. The mobile device 400 may provide many and various indications of activity to the user 404 and/or may provide many and various indications of how the activity corresponded to the activity expected by the mobile device 400.

The mobile device 400 may detect a user's 404 inhalation and/or exhalation 420 upon the acoustic signal produced as a result of the user's 404 inhalation and/or exhalation 420. The mobile device 400 may detect the user's 404 inhalation and/or exhalation 420 upon the mobile device 400 providing a cue to the user 404 to perform such activity. Upon receiving the acoustic signals representing a user's 404 exhalation and/or inhalation 420, mobile device 400 and/or sensing device may convert the user's 404 exhalation and/or inhalation 420 (e.g., acoustic signals of the user's 404 exhalation and/or inhalation 420) into electronic signals.

The duration and/or magnitude of a user's 404 inhalation and/or exhalation 420 may be determined by capturing the audio received by the microphone 410, and/or by performing low-pass filtering to isolate the sound associated with the user's 404 breath. The resultant energy (i.e., RMS (root-mean-squared) values) may be sampled over the received audio to determine an airflow profile. Higher RMS values may correspond to stronger inhalation and/or exhalation. Likewise, lower RMS values may correspond to less strong inhalation and/or exhalation. A longer duration profile between normative RMS values, measured higher RMS values, and back to normative RMS values may correspond to a longer duration inhalation and/or exhalation. Likewise, a shorter duration profile between normative RMS values and the measured higher RMS values and back to normative may correspond to a shorter duration inhalation and/or exhalation. The particular RMS values and normative thresholds may be calibrated in accordance with the mobile device's 400 specific hardware and Operating System (OS) Application Programing Interface (API). For example, functionality available in the AVAudioRecorder class in the Apple iOS™ operating system for iPhone™ may be used to capture audio, filter, and/or measure the resultant energy. This calibration may be done to determine the profile values appropriate for adequate inhalation and/or exhaling when dispensing medicament from certain inhalers.

The ways in which a user 404 may interact with the mobile device (e.g., for training purposes) may vary according to the medicament dispenser to be simulated. For example, while a user 404 of a simulated medicament dispenser in the form of an inhaler may allow a user 404 to breathe into the mobile device 400, a user 404 of simulated medicament dispenser in the form of a pill bottle may allow a user 404 to view instructions for opening and/or closing the pill bottle.

The mobile device and/or sensing device may be configured to process simulated dispensing data in accordance with predetermined data (e.g., a predetermined profile) so as to generate assessed data. The mobile device and/or sensing device may be configured to monitor an action performed upon the mobile device and/or sensing device by a user so as to generate the dispensing data. The mobile device and/or sensing device may be configured to monitor an action performed upon the mobile device and/or sensing device by a user that is analogous to, and/or representative of, an action forming part of a mode in which the simulated medicament dispenser may be operated by a user. The predetermined data and/or predetermined profile may include data representative of an optimal mode and/or an ideal usage technique and/or pattern in which a medicament dispenser may be operated by a user. The predetermined data and/or predetermined profile may be downloaded data, and/or may have been prescribed by a medication provider or medical professional. For example, when the technique is adhered to by a user it optimizes the effectiveness of the dispensed medicament. The generating of the assessed data may include evaluating a relationship between the dispensing data and/or the predetermined data. The mobile device and/or the sensing device, which may take the form of electronic components within the dispenser, may be configured to compare the user's technique, represented by the dispensing data, with the ideal profile in order to evaluate user performance and provide appropriate constructive feedback.

The mobile device may be configured to present data (e.g., dispensed data, assessed data) and/or information including an evaluation of the monitored administering technique, to a user. The data may be presented by way of visual, audible, and/or haptic feedback. For example, the data may be presented via display. The assessed data may be presented by way of graphical representations, textual data, and/or numerical data. The data may be presented to users (e.g., doctors or other healthcare personnel, and/or parents of patients) other than patients, via electronic communications. The assessed data may be included in email, SMS, MMS, VOIP, and/or other electronic message or document formats and transmitted via the Internet or mobile communication networks. This sharing of feedback with patients and/or other parties may be advantageous to the providing of training. Data based upon the dispensing, predetermined, and/or assessed data may be stored in the sensing device. The mobile device and/or the sensing device may comprise a programmable memory for storing this information.

The mobile device may comprise a communication device (e.g., communication device 104). The communication device may comprise electrical connectors, transmitters, and/or receivers capable of communicating via electromagnetic signals. The signals may be communicated via wire, and/or the signals may be communicated wirelessly. The communication device may comprise internal connections (e.g., between various electronic components) and/or external communication devices that allow the system to communicate data with external parties or devices. The communication device may provide evaluation results to user. Evaluation results may be provided to the user as visual, audio, etc. feedback. The feedback may be positive feedback, constructive feedback, and so forth.

Pictorial, video, verbal, and/or textual guidance (e.g., guidance relating to administering the medicament) may be provided. As shown in FIG. 4, evaluation results may include a simple checkmark 415, indicating proper usage. Evaluation results may include detailed instructions for use of the simulated medicament dispenser. For example, evaluation results may indicate how the user properly used the simulated medicament dispenser, how the user improperly used the mobile device (e.g., the user breathed at an incorrect angle, the user placed a finger over the microphone when breathing proximate to the microphone, etc.). The mobile device may provide suggested actions (e.g., the user should breathe at a right angle of the microphone, etc.) for optimally using the mobile device 400 simulating the simulated medicament device. The evaluation results may be presented to the user via a display.

By monitoring a user's interactions with a medicament dispenser (e.g., the on-screen representation of a medicament dispenser (e.g., an inhaler)), correct techniques for using a dispenser may be provided. For example, the mobile device may be configured to present the user with information regarding differences between, and comparative advantages of, different types of dispenser devices. The mobile device may present the user with different techniques for different medicament dispensers. For example, the mobile device may indicate to a user that the activity performed upon a mobile device would be optimal for one medicament dispenser, but not for another medicament dispenser. This may allow a user to determine whether one medicament dispenser is better suited for the user's needs and/or abilities than another medicament dispenser. This information may be in the form of a video, instruction (e.g., step-by-step instructions), and so forth. Similar recording and/or evaluation of user actions with respect to predetermined data (e.g., data representing optimal and/or prescribed dispenser use) may be performed by the mobile device in response to various user actions.

Figure 5:
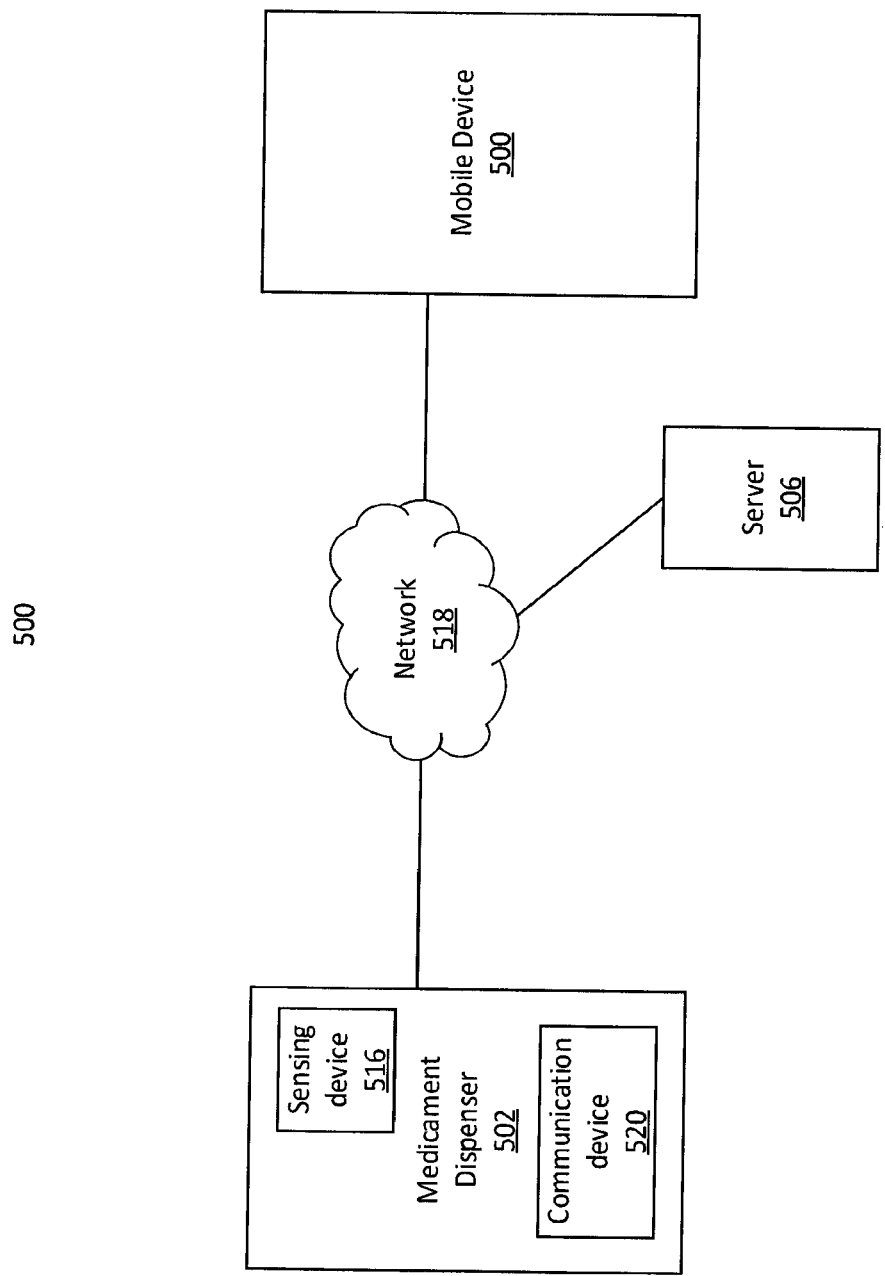
FIG. 5 is a block diagram of a computing network system 500

FIG. 5 illustrates a block diagram of a computing network system 500. As shown in FIG. 5, a medicament dispenser 502 and/or a mobile device 500 may be provided. The computing network system 500 may include one or more mobile devices 500 that may be capable of communicating digital messages with one another, either directly or via the network 518. The mobile device 500 may be a user device capable of logging into a session of an interactive computing environment and providing real-time interactive data via the network 518. The network 518 may include a wired and/or wireless network. For example, the network 518 may include a Wi-Fi communication network, a Wi-MAX communication network, a cellular communication network (e.g., CDMA, HSPA+, LTE, etc.), and/or a television white space (TVWS) communication network. The network 518 may include one or more communication networks.

The medicament dispenser 502 may include medicament, and/or the medicament dispenser 502 may not include medicament. The medicament dispenser 502 may be used for training purposes. For example, the medicament dispenser 502 not containing medicament may be provided to train a user how to use the device, without medicament being dispensed. This may be advantageous because it may allow a user to repeatedly practice the medicament dispensing activity, without medicament being released during each practice attempt.

Digital messages may be communicated between medicament dispenser 502 (e.g., an inhaler) and mobile device 500. The mobile device 500 and/or the medicament dispenser 502 may be capable of monitoring the administering (e.g., actual and/or simulated administration) of a medicament from medicament dispenser 502. The mobile device 500 may monitor the user's operation of the medicament dispenser 502. This may be achieved, for example, by attaching the dispenser 502 to the mobile device 500 and/or administering the medicament dispenser 502 in sufficiently close proximity to the mobile device 500 (e.g., for the mobile device's 500 optical, acoustic, and/or other sensors to monitor the use of the medicament dispenser 502).

A sensing device 516 may be integrated into the medicament dispensing device 502, and the sensing device 516 may be external to the medicament dispenser 502. The sensing device 516 may be configured to monitor an action performed upon the medicament dispenser 502 by a user. The sensing device 516 may monitor a user's actions upon the medicament dispenser 502. Such actions may include the sensing device 516 and/or medicament dispenser 502 being oriented in a particular manner; an acceleration being applied to the sensing device 516 and/or the medicament dispenser 502; a quantity of medicament being dispensed; and/or a rate at which medicament is being dispensed. The user's technique may be captured by the sensing device 516 and/or the medicament dispenser 502, and the technique may be recorded as dispensing data.

The sensing device 516 of the medicament dispenser 502 may be configured to transmit data, e.g., based upon the dispensing data, to the mobile device 500. The sensing device 516 may be configured to perform this transmission via a communication device 520. The communication device 520 may be integrated within sensing device 516, and/or the communication device 520 may be external to sensing device 516. The communication device 520 may include a wireless transmitter and/or receiver, and/or an electrical connector. This may allow the sensing device 516, and/or the dispenser 502, to upload or transmit user or dispensing data via being plugged into another mobile device and/or via wireless channels, e.g., depending upon the available hardware components and requirements.

Communication between the medicament dispenser 502 and the mobile device 500 may be via any of several wireless standards of which smartphones are typically capable, such as Bluetooth®, Bluetooth® Low Energy, infrared, cellular data, or Wi-Fi. The dispenser may include an electrical connector capable of interfacing with a smartphone connector socket, e.g., to transmit data over a wired connection. The wireless transmission of dispensing data from the medicament dispenser 502 to the mobile device 500 may be direct and/or indirect (e.g., may include a server, such as a web server 506). The server 506 may receive, store, process, and/or transmit dispensing data between the medical dispenser 502 and the mobile device 500 via the Internet. The server 506 may be configured to handle data pertaining to multiple medicament dispensers 502, mobile devices 500, users, care providers, medical patient accounts, and the like.

The medicament dispenser 502 may monitor and/or transmit the dispensing data to the mobile device 500 (e.g., in real time) so as to present to the user a live depiction of their inhaling technique and/or progress. The sensing device 516 of the medicament dispenser 502 may store the dispensing data and/or process or transmit the dispending data at a later time. Evaluation of the dispensing data may be performed by the mobile device 500 and/or the medicament dispenser 502. The assessed data may be transmitted among the mobile device 500, medicament dispenser 502, and/or server 506, and the assessed data may be presented to the user by one or more of those devices.

The medicament dispenser 502 and/or the sensing device 516 may transmit recorded (e.g., raw recorded) and/or dispensing data (e.g., monitored dispensing data) to the mobile device 500 and/or via a computer (e.g., Internet) server 506. The dispensing data may be formatted, refactored, compressed, and/or collated prior to transmission depending upon the physical capabilities of the system and/or the requirements of the specific application.

The sensing device 516 may be configured to monitor the medicament dispensing device 502 in use. The dispensing data captured by the sensing device 516 may include, for example, acoustic, chronological, pressure, location, temperature, optical, acceleration, and/or chemical data. The selected types and configurations of the sensors in the dispenser 502 may vary with different dispensers 502 and/or applications (e.g., so as to be able to obtain information indicating whether the dispenser is being used correctly and/or effectively).

The mobile device and/or medicament dispenser may be combined with an external sensor device. The external sensing device may be configured to be attachable to, and/or compatible with, the mobile device and/or the medicament dispenser. Electronic data may be exchanged between the devices via a communications interface. The external devices may provide functionality to the medicament dispenser, mobile device, and/or sensing device. The external devices may include a sensing device and/or components of the sensing device. For example, external sensors may be configured to monitor the use of the dispenser. One or more applications may be configured to receive data from the external and/or integrated sensors.

Figure 6:
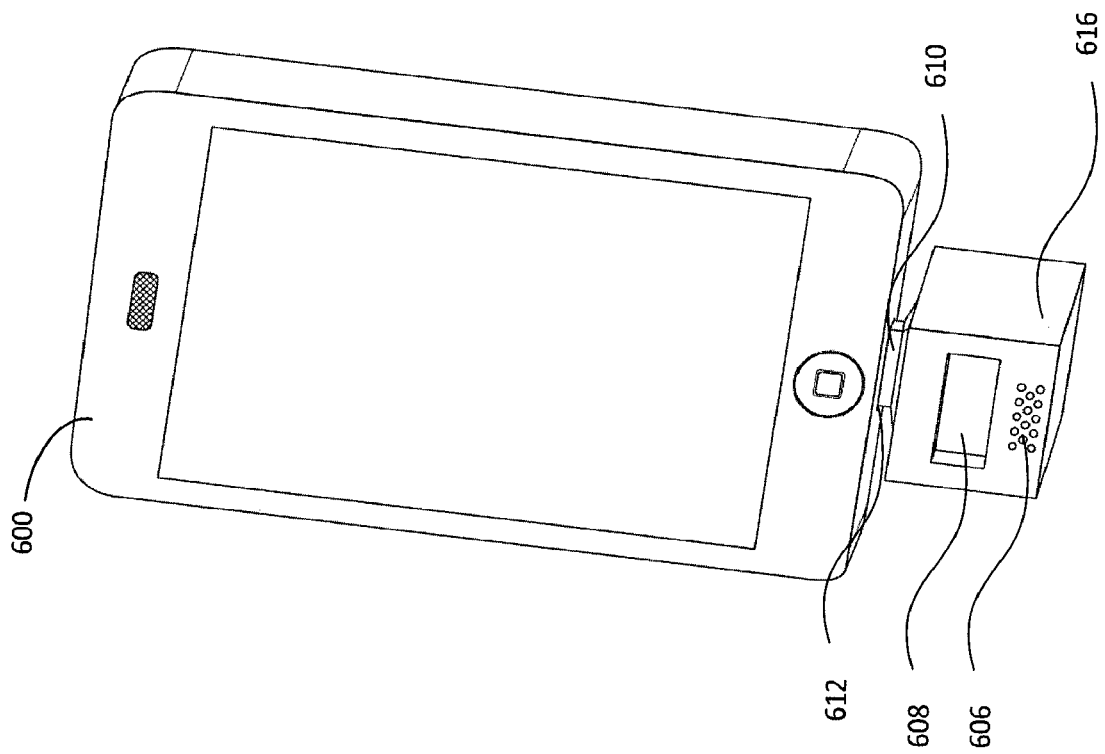
FIG. 6 is an example peripheral device coupled to an example mobile device.

FIG. 6 shows an example sensing device 616 that may be external from the mobile device 600. The external sensing device 616 may comprise a communications interface (e.g., an interface in the form of an electrical connector 610), which may be configured to be compatible with the connector socket 612 of the mobile device 600. Electronic data may be communicated between the mobile device 600 and the external sensing device 616, e.g., when a connection is made between the mobile device 600 and the external sensing device 616.

The external sensing device 616 may include various types of sensors 606. The sensors 606 may be configured to monitor user actions (e.g., user actions that recreate actions executed when operating a medicament dispenser). The attachment of the external sensing device 616 may allow the mobile device 600 and/or dispensing device to simulate additional medicament dispensers. For example, a mobile device 600 and/or dispensing device may not have pressure sensor functionality. An external sensing device 616 may comprise a pressure sensor 608. The pressure sensor 608 may monitor and/or record the air pressure resulting from a user inhaling and exhaling into the external sensing device 616 and/or dispensing device. The monitoring of fluid pressure instead of, or in addition to, the sound resulting from a user's breathing may provide higher quality data and/or data that is more relevant and/or a more accurate representation of the user's operation of an inhaler. By attaching an external sensor device 616 having a pressure sensor 608 to the mobile device 600 and/or dispensing device, the mobile device 600 and/or dispensing device may be capable of simulating medicament dispensers having, and/or requiring a pressure sensor, e.g., for simulation purposes.

Figure 7A:
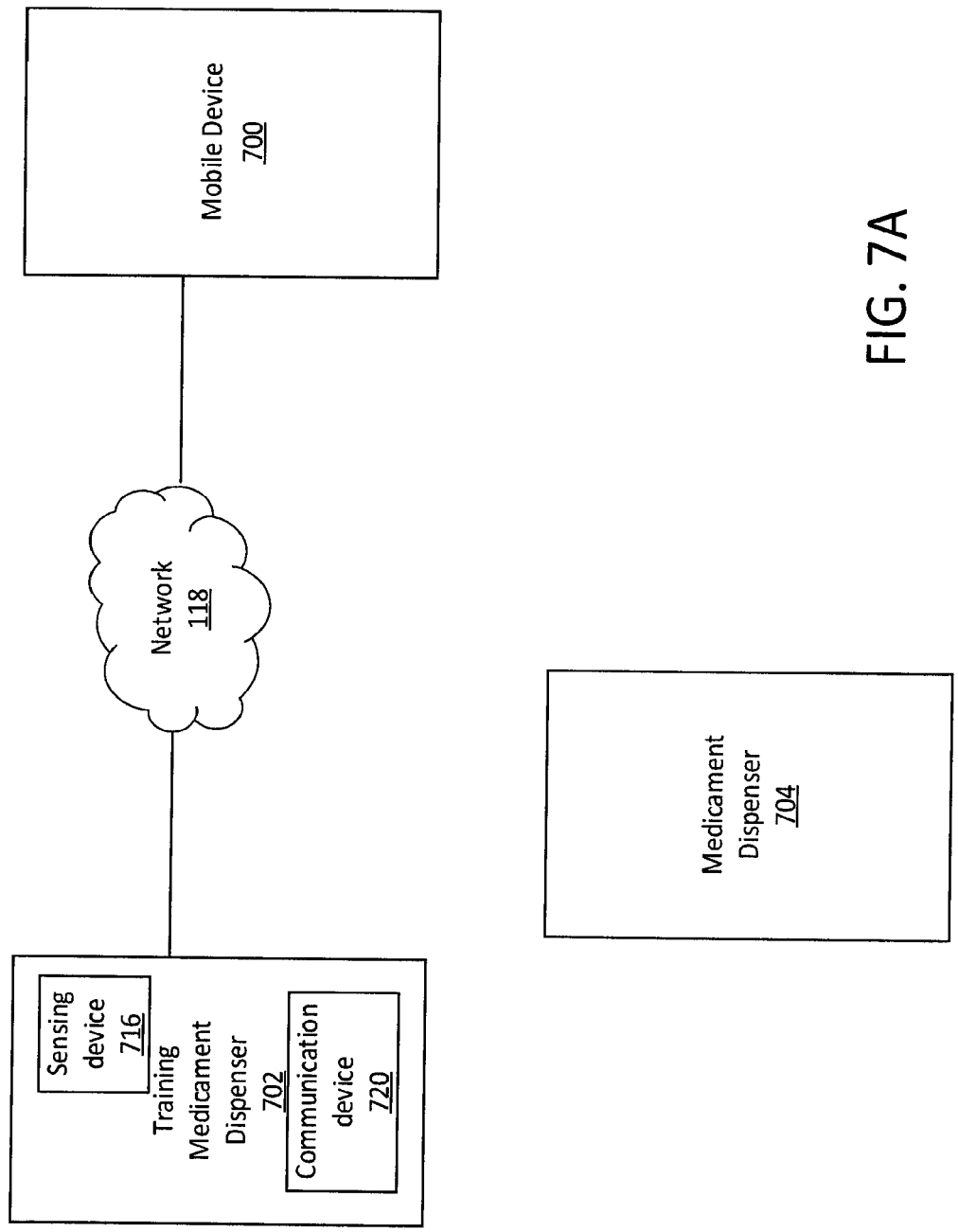
FIG. 7A illustrates an example system including a medicament dispenser and a training dispenser.

FIG. 7A shows an example system including a medicament dispenser 704 containing medicament, and a training medicament dispenser 702 not containing medicament. The medicament dispenser 704 may be used for distributing medicament to a user, and the training medicament dispenser 702 may be used for training purposes, e.g., to train a user in dispensing a medicament. The training medicament dispenser 702 may be used to train a user in the procedure of a medicament dispensing device, using a device having a housing that is the same, and/or similar, to medicament dispenser 704. The training medicament dispenser 702 may communicate with a mobile device 700, as described herein.

Figure 7B:
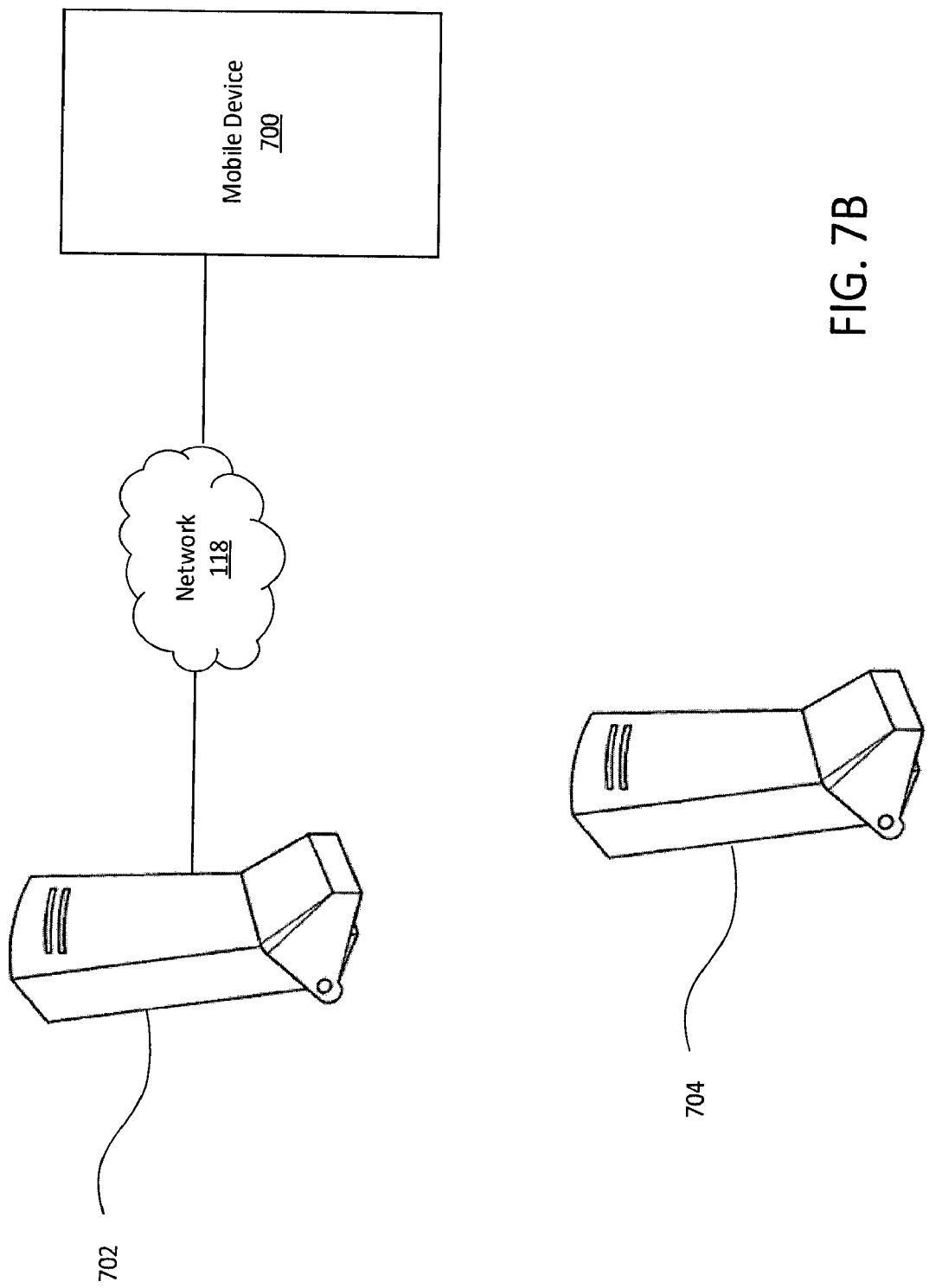
FIG. 7B illustrates an example system including a medicament dispenser having an inhaler housing and a training dispenser having an inhaler housing.

The medicament dispenser 704 and the training medicament dispenser 702 may have the same, and/or different, housings. For example, both the medicament dispenser 704 and the training medicament dispenser 702 may have inhaler housings, such as a Spiromax housing, shown on FIG. 7B. The medicament dispenser 704 may have a Spiromax housing, and the training medicament dispenser 702 may have an Easy-Breathe housing. The medicament dispenser 704 and the training medicament dispenser 702 may comprise the same, and/or different, electronics, sensing devices (e.g., sensing device 716), communication devices (e.g., communication device 720), and so forth. The medicament dispenser 704 and the training medicament dispenser 702 may comprise the same, and/or different medicament. The medicament dispenser 704 may comprise a medicament, and/or the training medicament dispenser 702 may not comprise a medicament. The training medicament dispenser 702 may substitute a medicament for a non-medicament substance. For example, training medicament dispenser 702 may substitute a medicament for a substance other than an active pharmaceutical ingredient (API). The medicament dispenser 704 and the training medicament dispenser 702 may comprise many, and various, components, housings, medicaments, non-medicaments, and the like.

The mobile device may simulate actions performed upon the medicament dispenser by way of a computer application running on the mobile device, medicament dispenser, and/or sensing device. A computer application may include a user playing games (e.g., a series of mini-games). The games may be centered upon simulating the use of various medicament dispensers (e.g., respiratory devices, such as inhalers). Tasks such as shaking the dispenser, exhaling from the dispenser, and/or on-screen interactions with the application may be included. The tasks may be included to help the user gain a better knowledge of the medicament dispenser, and/or to exhibit differences between types of medicament dispensers. In-game achievements, scheduled reminders, and/or helpful feedback related to the user's performance may be provided. The in-game achievements, scheduled reminders, and/or helpful feedback may provide a user with incentives for repeated use and/or rewarding users for progress made. Monitored dispensing data and/or connectivity capability may provide tips and/or information to the user, e.g., so clear and comprehensible training information may be provided.

The user may select to test themselves on the correct use of a device. For example, the mobile device and/or the medicament dispenser may enable the user to perform the actions they believe are correct for the device (e.g., by interacting with an onscreen simulation and/or with an actual dispenser). Once the challenge is complete, the mobile device and/or the medicament dispenser may present the user with a score, or other achievement feedback. The score may be based upon how many of the user's actions were performed correctly, which may be based upon the predetermined correct user profile data.

Concepts drawn from psychology, software user experience, and/or the gaming industry may be provided, e.g., to improve the effectiveness with which feedback and/or training information may be presented to users and/or assimilated by users. Game playing may be provided to the user in accordance with the dispensing and/or assessed data. The game playing may be provided to encourage increased practice and/or training so as to increase user proficiency with dispensing devices. The mobile device may contain software configured to gamify various aspects of using the dispenser by including such elements. These aspects may include gaming features such as point-scoring, rewards, "unlockable" content, one or more achievement badges, levels of progression, progress bars, ratings, and/or rankings. These may be presented to the user in accordance with the monitored relationship between the dispensing data and/or predetermined data.

Figure 8B:
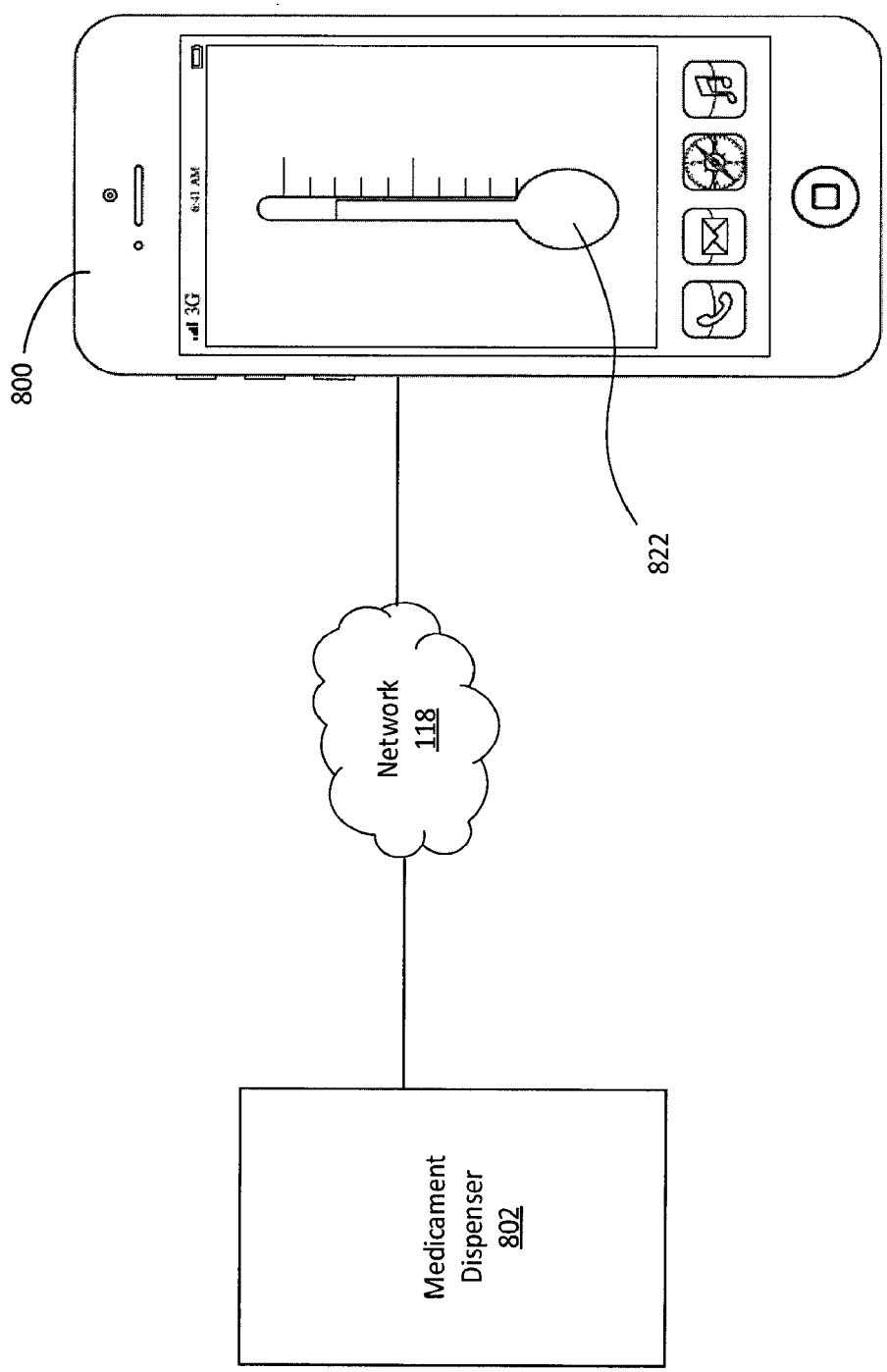
FIG. 8B illustrates another example use of a medicament dispenser providing input illustrated by an example GUI on the mobile device.

FIGS. 8A-8E illustrate example styles of presenting information to a user, e.g., based upon the dispensing or assessed data. The activity of dispensing medicament may be presented by the mobile device 800 as a game. For example, the activity of dispensing inhaler medicament may be visualized by the mobile device 800 as an on-screen representation of a user's progress in breathing. A user's breathing may be monitored by the mobile device 800, and the breathing of the user may drive a visualized filling and/or inhalation of a target. For example, as shown in FIG. 8A, the breathing of a user may be visualized as a blowing up and/or deflating of a blowfish 820. As the user inhales and/or exhales about the medicament dispenser, the volume of the blowfish 820 may decrease and/or increase. As shown on FIG. 8B, the visualized filling of a meter 822 (e.g., a thermometer) and/or inflation of a target may correlate with an administration of a medicament. The visualized filling of the meter 822 and/or inflation of an object may present a target for a user to obtain, e.g., to obtain optimal medicament dispensing. The visualization of data on the mobile device 800 and/or interaction with the medicament dispenser 802 may be incorporated into a wide variety of game mechanics.

Figure 8C:
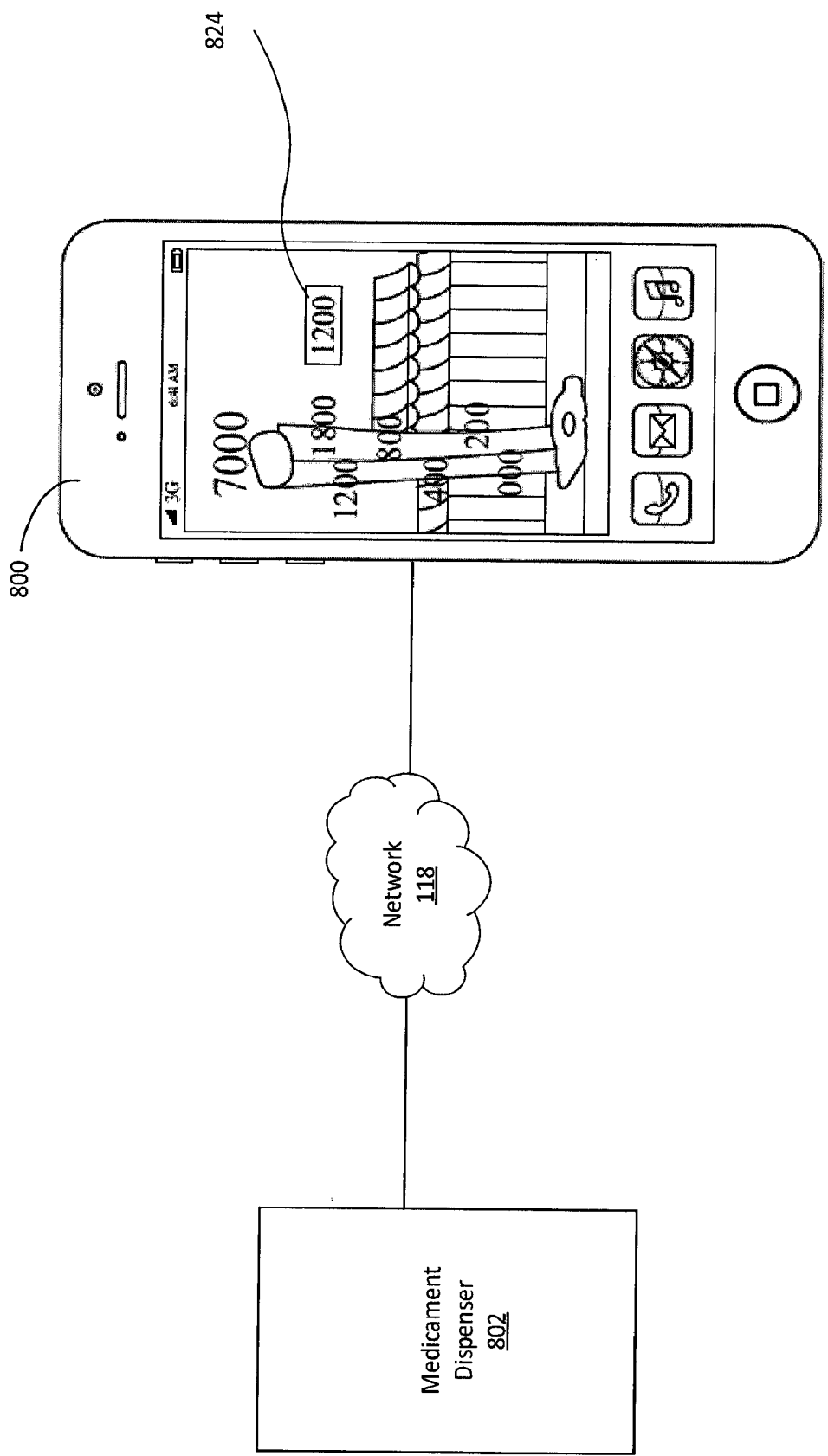
FIG. 8C illustrates yet another example use of a medicament dispenser providing input illustrated by an example GUI on the mobile device.

FIG. 8C shows an example wherein a user may score points based on a use of the medicament dispenser 802. For example, a score 824 of the user may increase and/or decrease, dependent on how the user is interacting with the medicament dispenser 802 and/or mobile device 800. As the user continues to improve upon medicament dispensing activities, the user's score 824 in the game may increase. The score 824 may be used to provide comparisons to users of previous medicament dispensing activities, and/or may provide a goal for the user to strive toward.

Figure 8D:
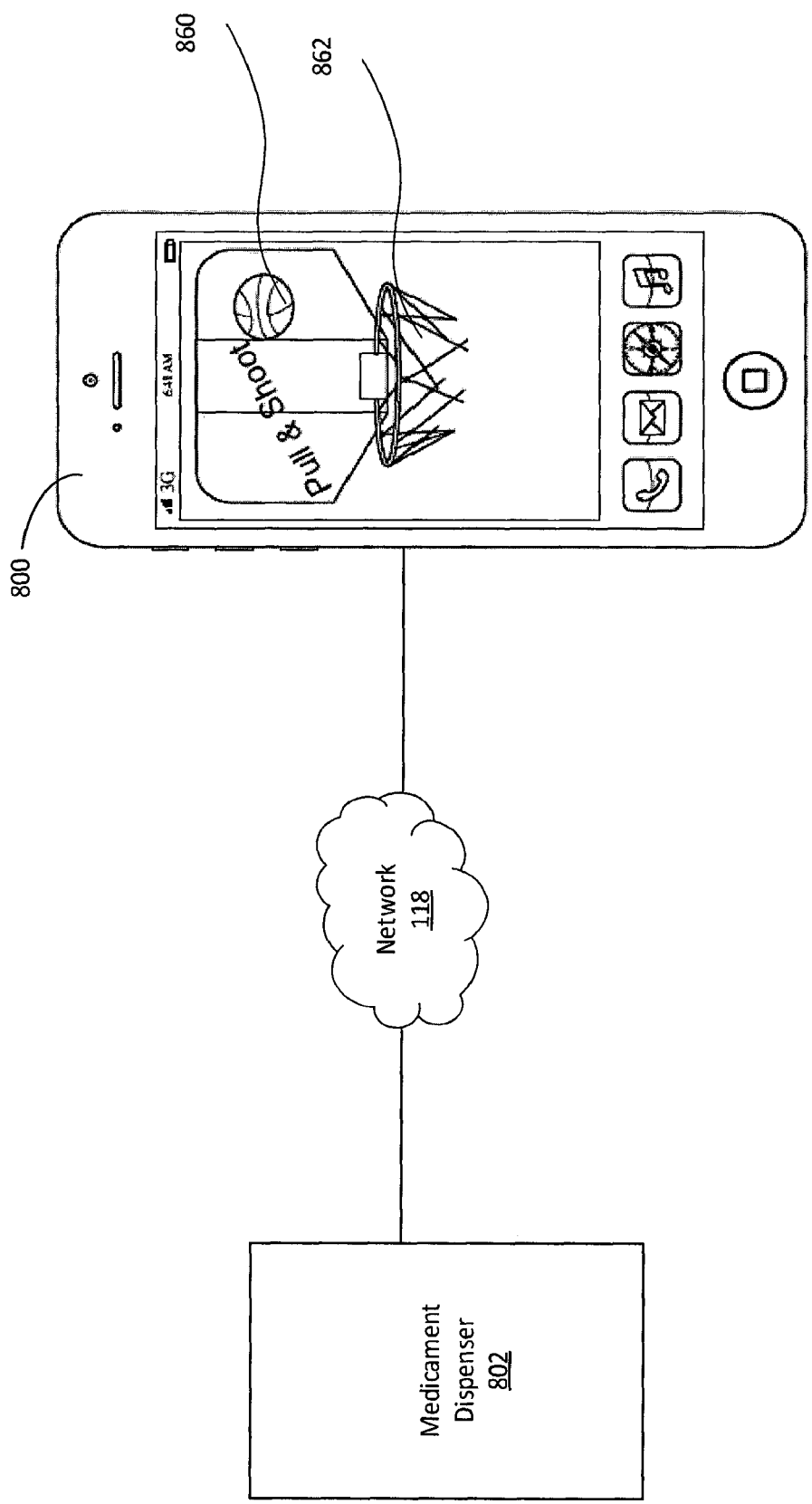
FIG. 8D illustrates yet another example use of a medicament dispenser providing input illustrated by an example GUI on the mobile device.
Figure 8E:
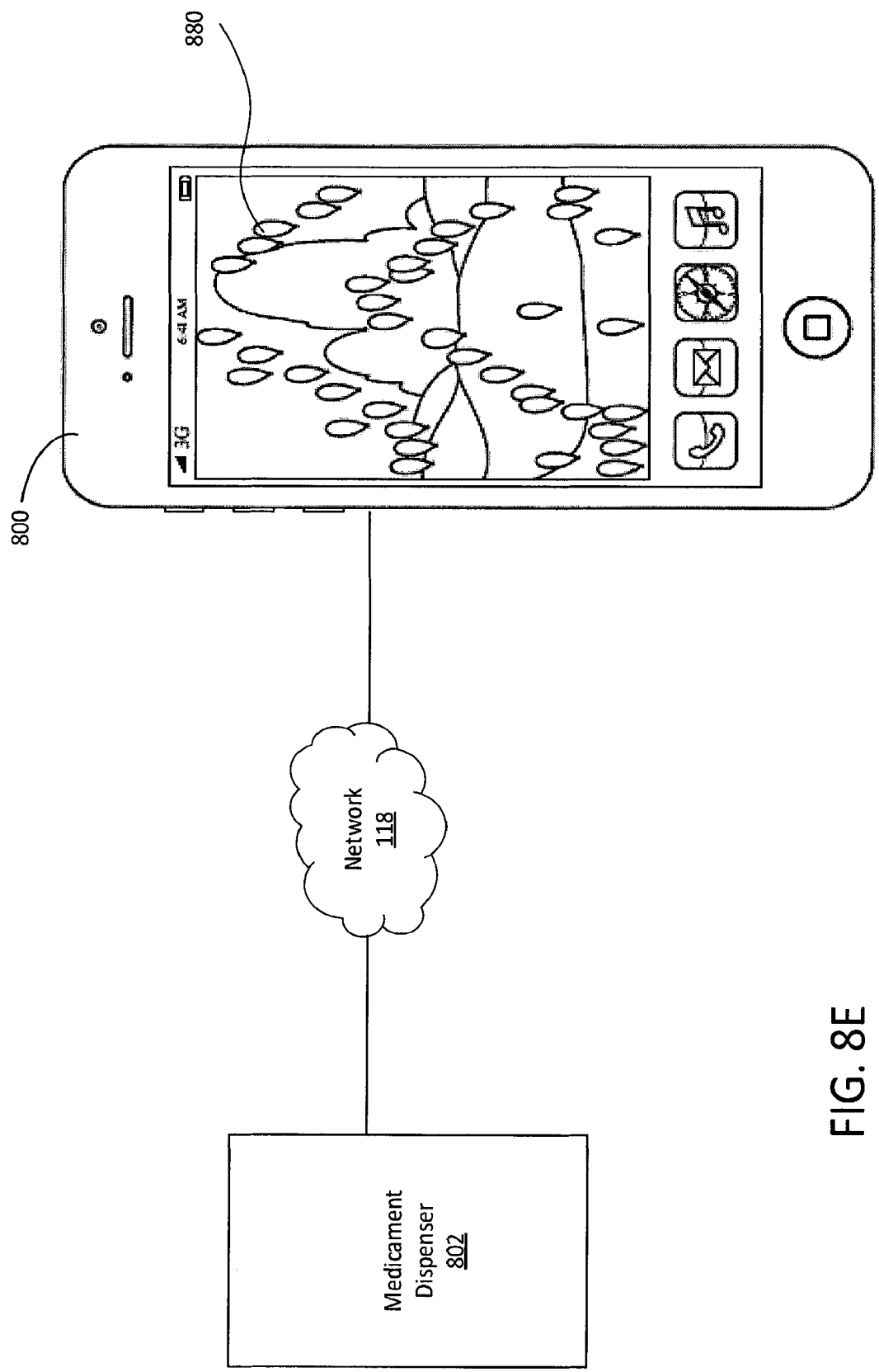
FIG. 8E illustrates yet another example use of a medicament dispenser providing input illustrated by an example GUI on the mobile device.

FIG. 8D shows an example wherein the mobile device 800 is running an application and the medicament dispenser's 802 use is represented as a basketball game. As the user exhales, the mobile device 800 may display the basketball 860 being drawn back. Upon the patient's inhaling of the medicament, the ball 860 may be shot towards the hoop 862. The degree to which the user exhales and/or inhales may correspond to ideal inhale and/or exhale. For example, the basketball 860 may reach its target if the user obtains optimal breathing techniques. FIG. 8E shows an example wherein the mobile device 800 is running an application and the medicament dispenser's 802 use is represented as flying balloons 880. The traveling of the flying balloons 880 may depend on the quality of the patient's inhalation and/or exhalation. The distance that the balloons 880 travel and/or the heights that the balloons 880 reach may depend on the quality of the patient's inhalation and/or exhalation. For example, an inhalation that corresponds to an optimal inhalation may result in the balloons 880 traveling further and/or higher than a suboptimal inhalation. Information related to the dispensing of medicament (e.g., information related to the inhalation technique used for a particular inhaler) may be visualized in numerous ways, including, for example, by charts, tables, and/or other graphics.

Figure 9:
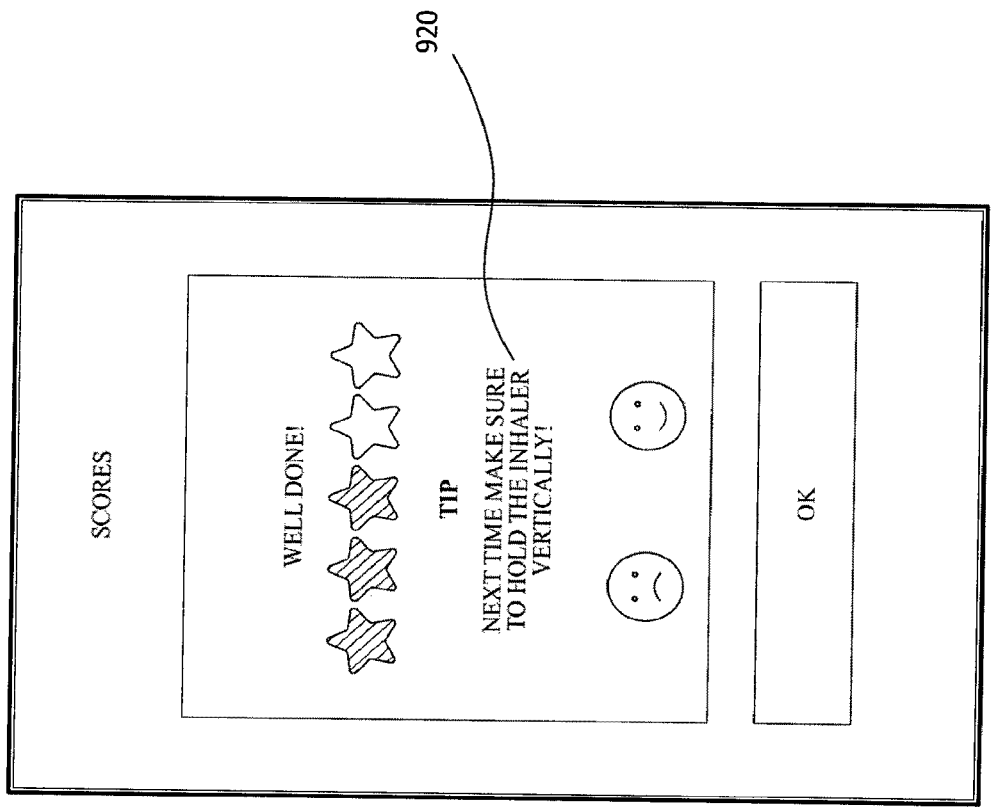
FIG. 9 illustrates an example GUI on a mobile device providing a score and guidance.

With reference to FIG. 9, the mobile device and/or medicament dispenser may provide the user with guidance 920, assistance, and/or score information 922. The guidance 922, assistance, score information 922 may be visualized in the form of a message delivered by a medical professional avatar, for example. The guidance 920, assistance, and/or score information 922 may be brief and/or detailed, depending on the needs of the user and/or the medical provider. Guidance may be generated in accordance with the user's past performance in the challenges and/or in accordance with the user's past performance in dispensing the medicament. The tips may, e.g., be presented in a manner to make the application have a personal touch to the individual user. The user may be presented with ratings according to the assessment of their actual or simulated dispenser use technique.

Various achievements may be provided within the application so as to encourage continued and correct game play. Examples of achievements might include completing all of the tasks, scoring a number of points, and/or using the application a number of times. The user may be given a specific set of goals to achieve and may be encouraged to play through the game in its entirety. Schedules may be generated and/or location-based reminders may be provided for the user to practice their technique with respect to the medicament dispenser. These reminders may be presented to the user via the mobile device 900 and/or the medicament dispenser 904. The occurrence of reminders may be based upon predetermined intervals, prescriptions or user-defined parameters.

Data generated by the mobile device and/or the medicament dispenser may be shared with medical care providers, medication providers, and the like. The data may be shared in real time, and/or by collecting and analyzing the data over a configurable period. The impact of the medicament upon a user's health outcome may be examined, e.g., based upon the efficacy of the medicament and/or the level of technical adherence and compliance of the patient in using it.

Figure 10:
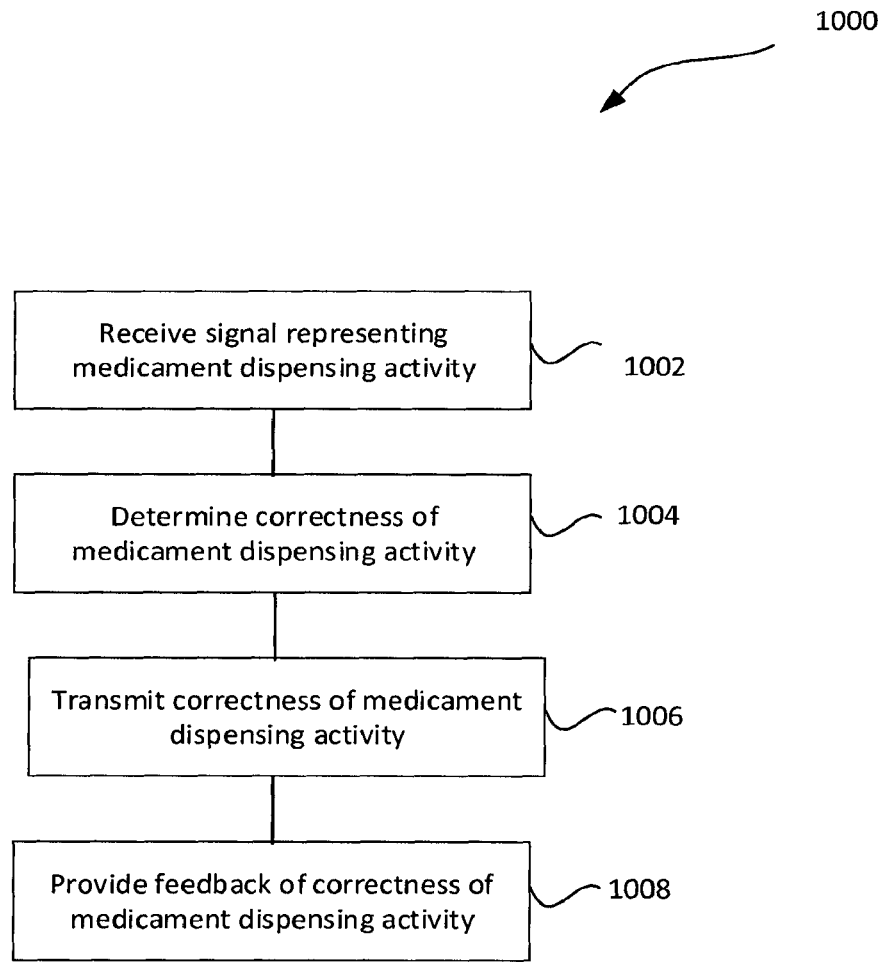
FIG. 10 is a flow diagram of an example method for receiving feedback as a result of simulating a medicament dispensing activity.

FIG. 10 is a simplified flow diagram depicting an example method for receiving feedback as a result of simulating a medicament dispensing activity. At 1002, a signal may be received. The signal may be received by the mobile device, sensing device, and/or a medicament dispenser. The signal may represent a medicament dispensing activity. For example, the signal may be representative of a technique with which a user administers a medicament from a medicament dispenser. The dispensing data may include data representing a physical action executed by a user in operating the medicament dispenser; a spatial orientation of the medicament dispenser; an acceleration applied to the medicament dispenser; a quantity of medicament dispensed; and/or a rate at which medicament is dispensed. The user's technique may be captured by the mobile device, sensing device, and/or recorded as dispensing data by, e.g., detecting and/or measuring data representing various physical properties.

At 1004, the correctness of the medicament dispensing activity may be determined. The dispensing data may be processed with respect to predetermined data. The predetermined data may include data representative of an optimal mode, usage, and/or pattern in which a medicament dispenser may be operated by a user. The predetermined data may be downloaded data, and/or may have been prescribed by a medication provider or medical professional (e.g., when the technique is adhered to by a user it optimizes the effectiveness of the dispensed medicament). The dispensing data may be evaluated against the predetermined data, to determine assessed data.

At 1006, data (e.g., medicament dispensing data, assessed data, etc.) may be transmitted. The data may be transmitted to and/or from the mobile device, medicament dispenser, and/or sensing device. The transmitted data may include recorded (e.g., raw recorded) data and/or dispensing (e.g., monitored dispensing) data. The dispensing data may be formatted, refactored, compressed, and/or collated prior to transmission depending upon the physical capabilities of the system and/or the requirements of the specific application.

At 1008, evaluation information (e.g., evaluation information of the monitored administering technique) may be presented. The data and evaluation information may be presented to a user, e.g., via the mobile device and/or medicament dispenser. The data and/or information may be presented by way of visual, audible, and/or haptic feedback. For example, the data and/or information may be presented by way of graphical representations, textual data, and/or numerical data. The data may be presented to users (e.g., doctors or other healthcare personnel, and/or parents of patients) other than patients, via electronic communications. The assessed data may be included in email, SMS, MMS, VOIP, and/or other electronic message or document formats and transmitted via the Internet or mobile communication networks.

The evaluation information may comprise tips, guidance, and/or assistance information. The tips, guidance, and/or other information may be visualized in the form of a message delivered by a medical professional avatar. The tips, guidance, and/or other information may be brief and/or detailed, depending on the needs of the user and/or the medical provider. The tips, guidance, and/or other information may, e.g., be presented in a manner to make the application have a personal touch to the individual user. The user may be presented with ratings according to the assessment of their actual or simulated dispenser use technique. The user may be given a specific set of goals to achieve and may be encouraged to play through the game in its entirety.

What is claimed is:

1. A system comprising:
   a computer application residing on a mobile device;
   a medicament-free device not containing medicament comprising:
      a housing;
      a wireless communication device;
      an acoustic sensor configured to output acoustic data indicative of a user's inhalation;
      an accelerometer configured to output movement data indicative of whether the medicament-free device was shaken before or during a user's action performed upon the medicament-free device;
      an orientation sensor configured to output orientation data indicative of an orientation of the medicament-free device during the user's inhalation; and
      a processor configured to receive the acoustic data, the movement data, and the orientation data, and cause the wireless communication device to transmit the acoustic data, the movement data, and the orientation data to the mobile device; and
   wherein the computer application is configured to:
      receive the acoustic data, the movement data, and the orientation data;
      cause the mobile device to display an indication of whether the medicament-free device was shaken before or during the user's action based on the movement data;
      cause the mobile device to display an indication of the user's inhalation based on the acoustic data; and
      cause the mobile device to display an indication of orientation of the medicament-free device based on the orientation data.

2. The system of claim 1, wherein the indication of orientation indicates whether the orientation of the medicament-free device was optimal or sub-optimal.

3. The system of claim 1, wherein the processor is configured to cause the wireless communication device to transmit the acoustic data to the mobile device in real-time; and
   wherein the computer application is configured to receive the acoustic data in real-time and cause the mobile device to display the indication of the inhalation of the user upon the medicament-free device in real-time.

4. The system of claim 1, wherein the indication of orientation comprises an instruction for correcting a non-optimal orientation of the medicament-free device.

5. The system of claim 1, wherein the acoustic data comprises an indication of a rate at which medicament would be dispensed from the medicament-free device if the medicament-free device comprised and dispensed medicament; and
   wherein the computer application is configured to, based on the acoustic data, cause the mobile device to display the a rate at which medicament would be dispensed from the medicament-free device if the medicament-free device comprised and dispensed medicament.

6. The system of claim 1, wherein the housing of the medicament-free device imitates the shape and appearance of an oral inhaler housing.

7. The system of claim 1, wherein the computer application is further configured to compare the acoustic data with predefined data indicative of a model user action associated with the medicament-free device, and wherein the indication comprises a result of the comparison.

8. The system of claim 1, wherein the computer application is configured to cause the mobile device to display a game that includes the indication of the inhalation of the user upon the medicament-free device.

9. The system of claim 1, wherein the orientation sensor is an accelerometer.

10. The system of claim 1, wherein the medicament-free device further comprises a pressure sensor that is configured to convert pressure into an electronic signal.

11. The system of claim 10, wherein the pressure sensor is configured to record the air pressure resulting from a user inhaling and exhaling into the medicament-free device.

12. The system of claim 1, wherein the medicament-free device further comprises a biological sensor configured to convert a biological response into an electronic signal.

13. The system of claim 1, wherein the medicament-free device is configured to transmit dispensing data to the mobile device, the dispensing data comprising location data.

14. The system of claim 1, wherein the medicament-free device is configured to transmit dispensing data to the mobile device, the dispensing data comprising temperature data.

15. A system comprising:
   a computer application residing on a mobile device;
   a medicament-free device not containing medicament comprising:
      a housing;
      a wireless communication device;
      a pressure sensor configured to output pressure data indicative of a user's inhalation;
      an accelerometer configured to output movement data indicative of whether the medicament-free device was shaken before or during a user's action performed upon the medicament-free device;
      an orientation sensor configured to output orientation data indicative of an orientation of the medicament-free device during the user's inhalation; and
      a processor configured to receive the pressure data, the movement data, and the orientation data, and cause the wireless communication device to transmit the pressure data, the movement data, and the orientation data to the mobile device; and
   wherein the computer application is configured to:
      receive the pressure data, the movement data, and the orientation data;
      cause the mobile device to display an indication of whether the medicament-free device was shaken before or during the user's action based on the movement data;
      cause the mobile device to display an indication of the user's inhalation based on the pressure data; and
      cause the mobile device to display an indication of orientation of the medicament-free device based on the orientation data.

16. The system of claim 15, wherein the pressure data comprises an indication of a rate at which medicament would be dispensed from the medicament-free device if the medicament-free device comprised and dispensed medicament; and wherein the computer application is configured to, based on the pressure data, cause the mobile device to display the a rate at which medicament would be dispensed from the medicament-free device if the medicament-free device comprised and dispensed medicament.

17. The system of claim 15, wherein the housing of the medicament-free device imitates the shape and appearance of an oral inhaler housing.

18. The system of claim 15, wherein the computer application is further configured to compare the pressure data with predefined data indicative of a model user action associated with the medicament-free device, and wherein the indication comprises a result of the comparison.

19. The system of claim 15, wherein the computer application is configured to cause the mobile device to display a game that includes the indication of the inhalation of the user upon the medicament-free device.

20. The system of claim 15, wherein the medicament-free device is configured to transmit dispensing data to the mobile device, the dispensing data comprising location data.

* * * * *